US010966943B2

(12) United States Patent
Kang et al.

(10) Patent No.: US 10,966,943 B2
(45) Date of Patent: Apr. 6, 2021

(54) METHODS AND COMPOSITIONS FOR TREATMENT OF ASTHMA OR PARKINSON'S DISEASE

(71) Applicant: InnoPharmaScreen Inc., Incheon (KR)

(72) Inventors: Incheol Kang, Incheon (KR); Jeseong Park, Incheon (KR)

(73) Assignee: INNOPHARMASCREEN INC., Incheon (KR)

( * ) Notice: Subject to any disclaimer, the term of this patent is extended or adjusted under 35 U.S.C. 154(b) by 0 days.

(21) Appl. No.: 16/562,136

(22) Filed: Sep. 5, 2019

(65) Prior Publication Data

US 2020/0078321 A1 Mar. 12, 2020

Related U.S. Application Data

(60) Provisional application No. 62/727,858, filed on Sep. 6, 2018.

(51) Int. Cl.
*A61K 31/155* (2006.01)
*A61K 31/47* (2006.01)
*A61P 11/06* (2006.01)
*A61K 9/00* (2006.01)

(52) U.S. Cl.
CPC ............ *A61K 31/155* (2013.01); *A61K 31/47* (2013.01); *A61P 11/06* (2018.01); *A61K 9/0053* (2013.01)

(58) Field of Classification Search
CPC .... A61K 31/155; A61K 9/0053; A61K 31/47; A61P 11/00
See application file for complete search history.

(56) References Cited

U.S. PATENT DOCUMENTS

| | | |
|---|---|---|
| 4,160,452 A | 7/1979 | Theeuwes |
| 4,256,108 A | 3/1981 | Theeuwes |
| 4,265,874 A | 5/1981 | Bonsen et al. |
| 5,230,884 A | 7/1993 | Evans et al. |
| 5,292,499 A | 3/1994 | Evans et al. |
| 5,348,730 A | 9/1994 | Greenleaf et al. |
| 5,811,127 A | 9/1998 | Milstein et al. |
| 6,290,987 B1 | 9/2001 | Modi |
| 6,294,153 B1 | 9/2001 | Modi |
| 6,309,671 B1 | 10/2001 | Foster et al. |
| 6,436,367 B1 | 8/2002 | Modi |
| 6,524,557 B1 | 2/2003 | Bäckström et al. |
| 6,632,456 B1 | 10/2003 | Bäckström et al. |
| 6,696,466 B1 | 2/2004 | Dunaway |
| 6,720,001 B2 | 4/2004 | Chen et al. |
| 6,923,988 B2 | 8/2005 | Patel et al. |
| 7,189,853 B2 | 3/2007 | Sundaram et al. |
| 7,417,149 B2 | 8/2008 | Turchetta et al. |
| 7,446,116 B2 | 11/2008 | Bartl et al. |
| 7,528,254 B2 | 5/2009 | Brand et al. |
| 7,544,805 B2 | 6/2009 | Alnabari et al. |
| 7,550,133 B2 | 6/2009 | Hale et al. |
| 7,553,853 B2 | 6/2009 | Overeem et al. |
| 7,560,559 B2 | 7/2009 | Chou et al. |
| 7,589,128 B2 | 9/2009 | Szabo et al. |
| 7,700,776 B2 | 4/2010 | Hung et al. |
| 7,754,240 B2 | 7/2010 | Staniforth et al. |
| 7,812,168 B2 | 10/2010 | Sterimbaum et al. |
| 7,829,716 B2 | 11/2010 | Overeem et al. |
| 8,007,830 B2 | 8/2011 | Down |
| 8,048,449 B2 | 11/2011 | Kashid et al. |
| 8,115,004 B2 | 2/2012 | Reddy et al. |
| 8,178,680 B2 | 5/2012 | Reddy et al. |
| 8,188,285 B2 | 5/2012 | Guillén et al. |
| 8,207,343 B2 | 6/2012 | Indukuri et al. |
| 8,211,405 B2 | 7/2012 | Mueller-Walz et al. |
| 8,216,613 B2 | 7/2012 | Gryczke |
| 8,217,174 B2 | 7/2012 | Lee et al. |
| 8,246,935 B2 | 8/2012 | Mueller-Walz et al. |
| 8,263,125 B2 | 9/2012 | Vaya et al. |
| 8,268,352 B2 | 9/2012 | Vaya et al. |
| 8,303,991 B2 | 11/2012 | Siegrist et al. |
| 8,367,834 B2 | 2/2013 | Indukuri et al. |
| 8,389,726 B2 | 3/2013 | Piccariello |
| 8,414,867 B2 | 4/2013 | Mueller-Walz et al. |
| 8,426,599 B2 | 4/2013 | Park et al. |
| 8,426,600 B2 | 4/2013 | Lee et al. |
| 8,450,491 B2 | 5/2013 | Suri et al. |
| 8,563,776 B2 | 10/2013 | Chandran |
| 8,575,194 B1 | 11/2013 | Schultz |
| 8,658,208 B2 | 2/2014 | Fujisaki et al. |
| 8,686,151 B2 | 4/2014 | Kwon et al. |
| 8,715,730 B2 | 5/2014 | Takaki et al. |

(Continued)

FOREIGN PATENT DOCUMENTS

| | | |
|---|---|---|
| EP | 1338272 A1 | 8/2003 |
| WO | 1990009781 A1 | 9/1990 |

(Continued)

OTHER PUBLICATIONS

Calderon et al. J. Allergy Clin. Immunol. Aug. 1991, p. 274 (Year: 1991).*
Srivastava et al. in Antimicrobial Agents and Chemotherapy, Jun. 1999, p. 1334-1339 (Year: 1999).*
Bleeker et al., "Evidence for Multiple Genetic Susceptibility Loci for Asthma," American Journal of Respiratory and Critical Care Medicine, 1997, vol. 156, pp. S113-S116, American Thoracic Society, New York, New York.
Busse et al., "Expert Panel Report 3 (EPR-3): Guidelines for the Diagnosis and Management of Asthma-Summary Report 2007," Journal of Allergy Clinical Immunology, 2007, vol. 120(5), pp. S94-S138.

(Continued)

*Primary Examiner* — Dennis Heyer
(74) *Attorney, Agent, or Firm* — Potomac Law Group, PLLC

(57) ABSTRACT

The present invention relates to methods and compositions comprising proguanil for treating asthma. The invention also relates to methods and compositions comprising proguanil for treating Parkinson's disease.

8 Claims, 21 Drawing Sheets

(56) References Cited

U.S. PATENT DOCUMENTS

| | | |
|---|---|---|
| 8,920,837 B2 | 12/2014 | Pilgaonkar et al. |
| 9,149,472 B2 | 10/2015 | Schultz |
| 9,283,192 B2 | 3/2016 | Mullen et al. |
| 9,408,806 B2 | 8/2016 | Jain et al. |
| 9,446,000 B2 | 9/2016 | Hashaikeh et al. |
| 9,487,487 B2 | 11/2016 | Simhadri et al. |
| 9,492,379 B2 | 11/2016 | Park et al. |
| 9,629,915 B2 | 4/2017 | Pilgaonkar et al. |
| 9,717,684 B2 | 8/2017 | Bhaysar et al. |
| 9,745,567 B2 | 8/2017 | Watson et al. |
| 9,877,971 B2 | 1/2018 | Zhao et al. |
| 9,884,014 B2 | 2/2018 | Venkatesh |
| 9,925,183 B2 | 3/2018 | May |
| 9,931,304 B2 | 4/2018 | Staniforth et al. |
| 9,949,934 B1 | 4/2018 | Zerbe et al. |
| 10,195,193 B2 | 2/2019 | May |
| 10,195,211 B2 | 2/2019 | Zhao et al. |
| 10,278,931 B2 | 5/2019 | Kang |
| 2001/0036481 A1 | 11/2001 | Basu et al. |
| 2001/0038824 A1 | 11/2001 | Horii et al. |
| 2002/0141945 A1 | 10/2002 | Foster et al. |
| 2003/0008013 A1 | 1/2003 | Robinson et al. |
| 2003/0053960 A1 | 3/2003 | Heijerman et al. |
| 2003/0165436 A1 | 9/2003 | Staniforth et al. |
| 2003/0232019 A1 | 12/2003 | Basu et al. |
| 2004/0018243 A1 | 1/2004 | Basu et al. |
| 2004/0115236 A1 | 6/2004 | Chan et al. |
| 2004/0265375 A1 | 12/2004 | Platteeuw et al. |
| 2010/0196471 A1 | 8/2010 | Jain et al. |
| 2011/0142914 A1 | 6/2011 | Persaud et al. |
| 2012/0110957 A1 | 5/2012 | Lee et al. |
| 2013/0116215 A1 | 5/2013 | Coma et al. |
| 2015/0322049 A1 | 11/2015 | Aigner et al. |
| 2016/0279071 A1 | 9/2016 | Park et al. |
| 2017/0114008 A1 | 4/2017 | Cho et al. |
| 2017/0119660 A1 | 5/2017 | Temtsin-Krayz et al. |
| 2018/0169091 A1 | 6/2018 | May |
| 2019/0070164 A1 | 3/2019 | Schultze |

FOREIGN PATENT DOCUMENTS

| | | |
|---|---|---|
| WO | 1991004011 A1 | 4/1991 |
| WO | 1996040089 A2 | 12/1996 |
| WO | 2000000176 A1 | 1/2000 |
| WO | 2000059475 A1 | 10/2000 |
| WO | 2001013891 A2 | 3/2001 |
| WO | 2001060341 A1 | 8/2001 |
| WO | 2001078694 A2 | 10/2001 |
| WO | 2001078696 A2 | 10/2001 |
| WO | 2002067902 A2 | 9/2002 |
| WO | 2002080884 A2 | 10/2002 |
| WO | 2003015750 A1 | 2/2003 |
| WO | 2003072080 A1 | 9/2003 |
| WO | 2003079885 A2 | 10/2003 |
| WO | 2007097936 A2 | 8/2007 |
| WO | 2016140633 A1 | 9/2016 |

OTHER PUBLICATIONS

Cookson, "The alliance of genes and environment in asthma and allergy," Nature, 1999, vol. 402(Supp), pp. B5-B11, Macmillan Magazines Ltd., London, United Kingdom.

Holloway et al., "The genetic basis of atopic asthma," Clinical and Experimental Allergy, 1999, vol. 29, pp. 1023-1032, John Wiley & Sons Ltd., Hoboken, New Jersey.

International Search Report and Written Opinon dated Jan. 2, 2020 in International Application No. PCT/IB2019/057502.

Kauffmann et al., "Epidemiologic Study of the Genetics and Environment of Asthma, Bronchial Hyperresponsiveness, and Atopy*," Chest, 2002, vol. 121(3), page Supplement 27S, Elsevier Inc., Amsterdam, Netherlands.

Koppleman et al., "Genetic and environment in asthma: the answer of twin studies," European Respiratory Journal, 1999, vol. 13, pp. 2-4, ERS Journals Ltd., Sheffield, United Kingdom.

* cited by examiner

METHODS AND COMPOSITIONS FOR TREATMENT OF ASTHMA OR PARKINSON'S DISEASE

CROSS-REFERENCE TO RELATED APPLICATIONS

This application claims the benefit of the filing date of U.S. Appl. No. 62/727,858, filed Sep. 6, 2018, which is herein incorporated by reference in its entirety.

FIELD OF THE INVENTION

The present disclosure relates to methods and compositions comprising proguanil for treating asthma. The present disclosure also relates to methods and compositions comprising proguanil for treating Parkinson's disease.

BACKGROUND OF THE INVENTION

Asthma is a chronic inflammatory disease of the lower respiratory tract characterized by airway hyperresponsiveness and mucous obstruction. Bronchial asthma is the most common chronic disease affecting children and young adults. There is strong evidence for a genetic component in asthma (Bleecker et al., Am. J. Respir. Crit. Care. Med., 156: S113-6 (1997); Kauffmann et al., Chest, 121 (3 Supp.): 27S (2002)). Multiple environmental factors are also known to modulate the clinical expression of asthma as well as the asthma-associated phenotypes: bronchial hyperresponsiveness, atrophy and elevated IgE (Koppelman et al., Eur. Resp. J., 13: 2-4 (1999); Cookson, Nature, 25: B5-11 (1999); Holloway, Clin. Exp. Allergy, 29: 1023-1032 (1999)).

Pharmacologic analogues of cortisol (e.g., prednisone) have been used clinically since 1948 and remain the standard of care for the treatment of a variety of inflammatory diseases including asthma. These glucocorticoids (GC) reduce pathological inflammation that is central to asthma, and they are thought to control clinical asthma symptoms through their anti-inflammatory effects (Expert Panel Report 3 (EPR-3): Guidelines for the Diagnosis and Management of Asthma-Summary Report 2007. J Allergy Clin. Immunol. 2007, 120:S94-138). There remains a need for improved methods for treating asthma.

Parkinson's disease is a disturbance of voluntary movement in which muscles become stiff and sluggish, movement becomes clumsy and difficult and uncontrollable rhythmic twitching of groups of muscles produces characteristic shaking or tremor. The condition is believed to be caused by a degeneration of pre-synaptic dopaminergic neurones in the brain. The absence of adequate release of the chemical transmitter dopamine during neuronal activity thereby leads to the Parkinsonian symptomatology.

The most widely used treatment for Parkinsonism is administration of L-DOPA, a precursor of dopamine which acts indirectly by replacing the missing dopamine. However, disadvantages are associated with the use of L-DOPA, for example, patients often suffer from side-effects such as dyskinesia and on-off effects, and it is necessary to administer L-DOPA in conjunction with a peripheral dopa-decarboxylase inhibitor such as carbidopa or benzaseride. These inhibitors prevent the peripheral degradation of levodopa to dopamine, thus enabling more drug to enter the brain and limiting peripheral side-effects. Such treatment improves quality of life for patients but does not halt disease progression. Furthermore, such treatment is associated with a number of adverse effects, including nausea, vomiting, abdominal distension and psychiatric side-effects (for example, toxic confusional state, paranoia, and hallucinations). There continues to be a need for improved treatments for Parkinson's disease.

BRIEF SUMMARY OF THE INVENTION

Disclosed herein is a method of treating asthma in a subject in need thereof, the method comprising administering to the subject a pharmaceutical composition comprising a compound represented by Formula 1 or a pharmaceutically acceptable salt thereof and a pharmaceutically acceptable excipient:

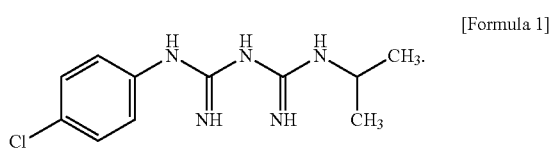

[Formula 1]

In some embodiments of the method, the composition further comprises a compound represented by Formula 2 or a pharmaceutically acceptable salt thereof:

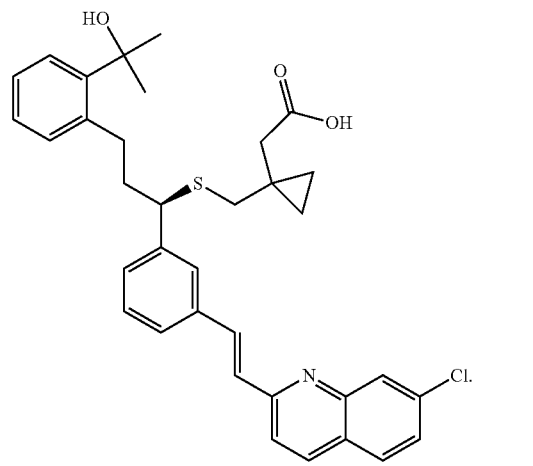

[Formula 2]

The asthma can be but is not limited to allergen-induced asthma, viral-induced asthma, cold-induced asthma, pollution-induced asthma and/or exercise-induced asthma.

In some embodiments of the method of treating asthma, the compositions are administered orally to the subject. In some embodiments of the method of treating asthma, the compositions comprise 0.001 mg to 100 mg of each of the compound per kg of the subject's body weight.

Also disclosed herein are pharmaceutical compositions comprising a compound represented by Formula 1 or a pharmaceutically acceptable salt thereof, a compound represented by Formula 2 or a pharmaceutically acceptable salt thereof, and a pharmaceutically acceptable excipient:

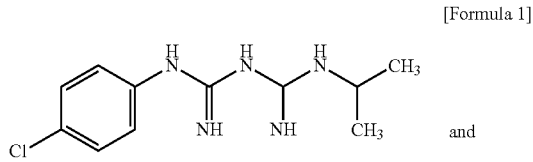

[Formula 1]

and

-continued

[Formula 2]

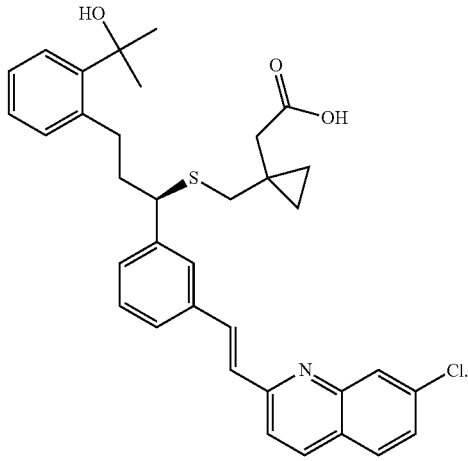

In some embodiments, the compositions are suitable for oral administration to subjects. In some embodiments, the compositions comprise 1 mg to 1000 mg of each of the compound.

Also disclosed herein is a method of treating Parkinson's disease in a subject in need thereof, the method comprising administering to the subject a pharmaceutical composition comprising a compound represented by Formula 1 or a pharmaceutically acceptable salt thereof and a pharmaceutically acceptable excipient:

[Formula 1]

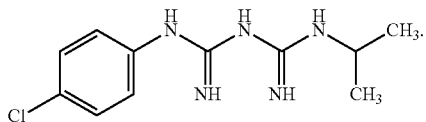

In some embodiments of the method, the composition further comprises a compound represented by Formula 2 or a pharmaceutically acceptable salt thereof:

[Formula 2]

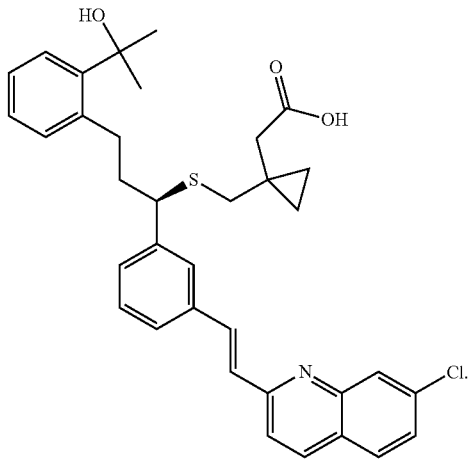

In some embodiments of the method of treating Parkinson's disease, the compositions are administered orally to the subject. In some embodiments of the method of treating Parkinson's disease, the compositions comprise 0.001 mg to 100 mg of each of the compound per kg of the subject's body weight.

DETAILED DESCRIPTION OF THE INVENTION

Figure 1:
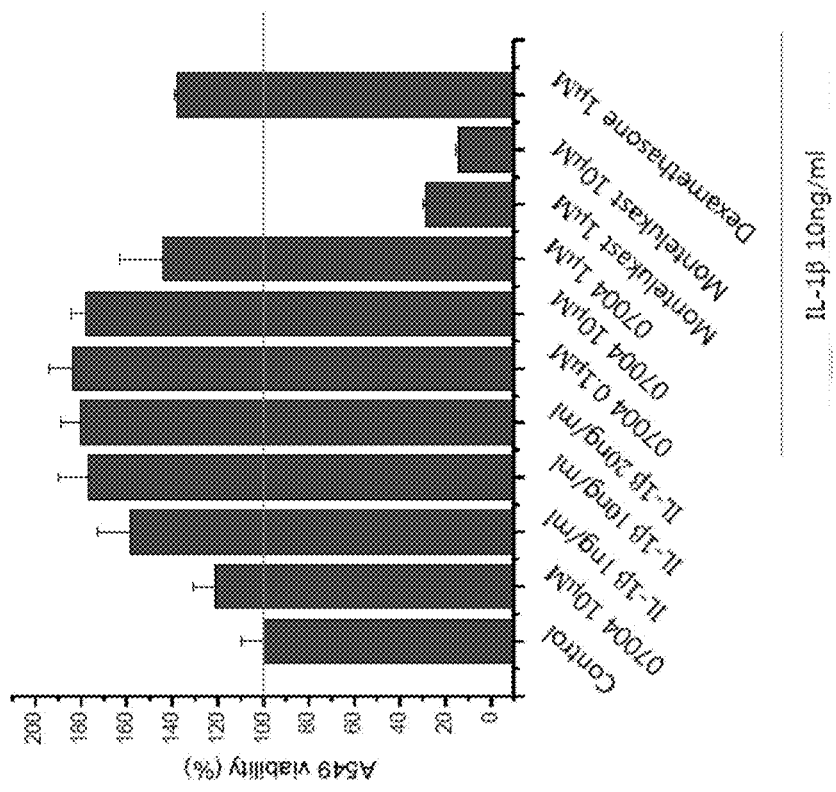
FIG. 1. Effect of IPS-07004 on the survival of A549 lung carcinoma cells.
Figure 1:
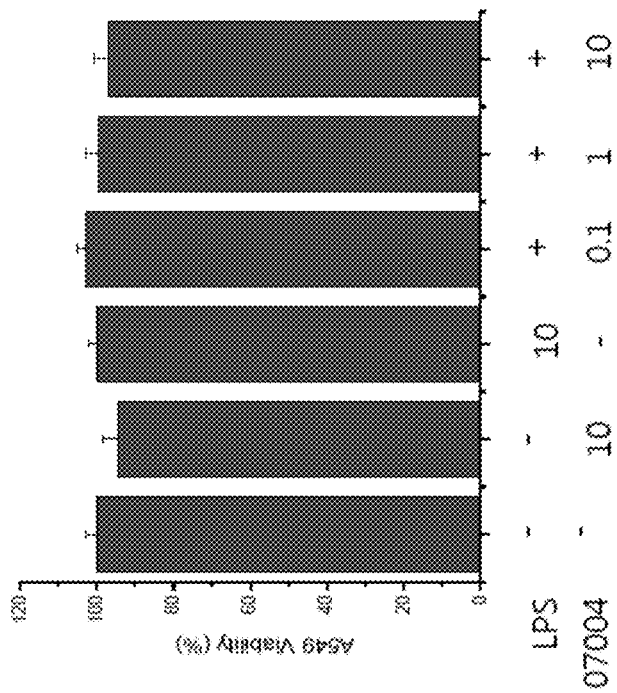

Proguanil, also known as chlorguanide, is a prodrug that is converted by the liver to its active metabolite, cycloguanil, an inhibitor of dihydrofolate reductase (DHFR). The present disclosure provides compositions comprising a compound represented by Formula 1 or a pharmaceutically acceptable salt thereof:

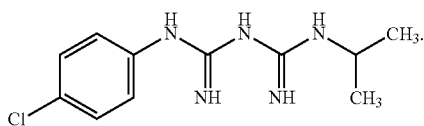

[Formula 1]

The compositions can further comprise montelukast (trade name SINGULAIR), a compound represented by Formula 2 or a pharmaceutically acceptable salt thereof:

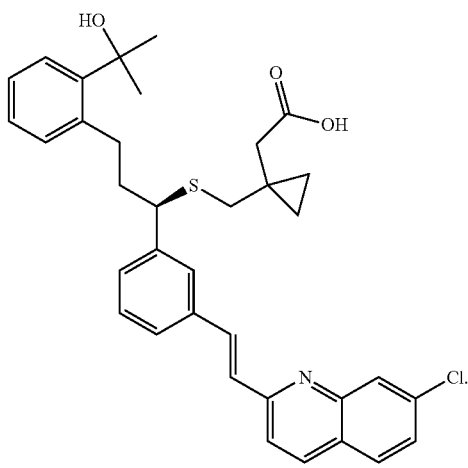

[Formula 2]

Montelukast is a leukotriene receptor antagonist (LTRA) used for the maintenance treatment of asthma and to relieve symptoms of seasonal allergies. Montelukast is a $CysLT_1$ antagonist; it blocks the action of leukotriene D4 (and secondary ligands LTC4 and LTE4) on the cysteinyl leukotriene receptor $CysLT_1$ in the lungs and bronchial tubes by binding to it. This reduces the bronchoconstriction otherwise caused by the leukotriene and results in less inflammation.

Montelukast is used for a number of conditions including asthma, exercise induced bronchospasm, allergic rhinitis, primary dysmenorrhoea (i.e., dysmenorrhoea not associated with known causes; see dysmenorrhea causes), and urticaria. It is mainly used as a complementary therapy in adults in addition to inhaled corticosteroids, if they alone do not bring the desired effect. It is also used to prevent allergic reactions and asthma flare-ups during the administration of intravenous immunoglobulin.

The compositions disclosed herein can comprise proguanil, proguanil and montelukast, or proguanil and other anti-asthma agents, such as zileuton, zafirlukast, terbutaline sulfate, and albuterol. The compositions disclosed herein can also comprise proguanil, montelukast and other agents for treating Parkinson's disease, such as L-DOPA, carbidopa, and/or benzaseride.

The pharmaceutically acceptable salts of the compounds disclosed herein include salts derived from inorganic bases such as lithium (Li), sodium (Na), potassium (K), calcium (Ca), magnesium (Mg), iron (Fe), copper (Cu), zinc (Zn), and manganese (Mn); salts of organic bases such as N,N'-diacetylethylenediamine, glucamine, triethylamine, chlorine, hydroxide, dicyclohexylamine, metformin, benzylamine, trialkylamine, thiamine, and equivalents thereof; chiral bases such as alkylphenylamine, glycinol, phenyl glycinol and equivalents thereof; natural amino acid salts such as glycine, alanine, valine, leucine, isoleucine, norleucine, tyrosine, cystine, cysteine, methionine, proline, hydroxyl proline, histidine, ornithine, lysine, arginine, serine, and equivalents thereof; quaternary ammonium salts of compounds of the present disclosure having an alkyl sulfate such as an alkyl halide, MeI, and $(Me)_2SO_4$ and equivalents thereof; artificial amino acids such as D-isomer, substituted amino acid, or the like; guanidine, guanine substituted with one selected from nitro, amino, alkyl, alkenyl, and alkynyl, ammonium or substituted ammonium salts, and aluminum salts. Salts can include acid-added salts, and examples of suitable salts include sulphates, nitrates, phosphates, perchlorates, borates, hydrohalides, acetates, tartrates, maliates, citrates, fumarates, succinates, palmoates, methanesulfonate, benzoate, salicylate, benzenesulfonate, ascorbate, glycerophosphate, ketoglutarate, and equivalents thereof. Pharmaceutically acceptable solvent compounds include crystallization solvents such as hydroxides or alcohols.

In addition to salt forms, the present disclosure provides compounds that are in a prodrug form. Prodrugs of the compounds described herein are those compounds that readily undergo chemical changes under physiological conditions to provide the compounds of the disclosure. Additionally, prodrugs can be converted to the compounds of the present disclosure by chemical or biochemical methods in an ex vivo environment. For example, prodrugs can be slowly converted to the compounds of the disclosure when placed in a transdermal patch reservoir with a suitable enzyme or chemical reagent. Prodrugs are often useful because, in some situations, they can be easier to administer than the parent drug. They can, for example, be bioavailable by oral administration whereas the parent drug is not. The prodrug can also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the disclosure which is administered as an ester (the "prodrug"), but then is metabolically hydrolyzed to the carboxylic acid, the active entity. Additional examples include peptidyl derivatives of a compound of the disclosure.

Certain compounds of the present disclosure can exist in unsolvated forms as well as solvated forms, including hydrated forms. In general, the solvated forms are equivalent to unsolvated forms and are intended to be encompassed within the scope of the disclosure. Certain compounds of the disclosure can exist in multiple crystalline or amorphous forms. In general, all physical forms are equivalent for the uses contemplated by the disclosure and are intended to be within the scope of the disclosure.

Certain compounds of the present disclosure possess asymmetric carbon atoms (optical centers) or double bonds; the racemates, enantiomers, diastereomers, geometric isomers and individual isomers are all intended to be encompassed within the scope of the disclosure. These isomers can be resolved or asymmetrically synthesized using conventional methods to render the isomers "optically pure," i.e., substantially free of its other isomers. For example, if a particular enantiomer of a compound of the present disclosure is desired, it can be prepared by asymmetric synthesis, or by derivation with a chiral auxilliary, where the resulting diastereomeric mixture is separated and the auxilliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatographic means well known in the art, and subsequent recovery of the pure enantiomers.

Compositions

Also disclosed herein are pharmaceutical compositions comprising a compound represented by Formula 1 or a pharmaceutically acceptable salt thereof, a compound represented by Formula 2 or a pharmaceutically acceptable salt thereof, and a pharmaceutically acceptable excipient:

[Formula 1]

and

[Formula 2]

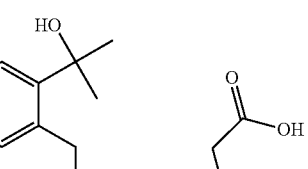

In some embodiments, the compositions are suitable for oral administration to subjects. In some embodiments, the compositions comprise 1 mg to 1000 mg of each of the compound.

In some aspects, the present disclosure provides pharmaceutical compositions suitable for pharmaceutical use comprising one or more compounds of the present disclosure and a pharmaceutically acceptable excipient or carrier. The compositions disclosed herein can comprise proguanil, proguanil and montelukast, or proguanil and other anti-asthma agents, such as zileuton, zafirlukast, terbutaline sulfate, and albuterol. The compositions disclosed herein can also comprise proguanil, montelukast and other agents for treating Parkinson's disease, such as L-DOPA, carbidopa, and/or benzaseride.

As used herein, "pharmaceutically acceptable" or "pharmacologically acceptable" mean molecular entities and compositions that do not produce an adverse, allergic or other untoward reaction when administered to an animal, or to a human, as appropriate.

The term, "pharmaceutically acceptable excipient or carrier" includes one or more inert excipients, which include starches, polyols, granulating agents, microcrystalline cellulose, diluents, lubricants, binders, disintegrating agents, and the like, and any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. "Pharmaceutically acceptable excipient" also encompasses controlled release means.

Formulations can improve one or more pharmacokinetic properties (e.g., oral bioavailability, membrane permeability) of a compound or combinations of compounds of the disclosure (herein referred to as the active ingredient(s)).

The composition, shape, and type of dosage form can typically vary according to applications thereof. For example, a dosage form suitable for mucosal administration can include a smaller amount of the active ingredient than that in a dosage form suitable for oral administration used in treating the same disease. These aspects of the present disclosure will be fairly apparent to those of ordinary skill in the art (reference: Remington's Pharmaceutical Sciences (1990) 18th ed., Mack Publishing, Easton Pa.).

Typical pharmaceutical compositions and dosage forms include one or more excipients. Suitable excipients are apparent to those of ordinary skill in the pharmaceutical art, and the present disclosure is not limited to examples of suitable excipients described herein.

Whether a particular excipient is suitable for a pharmaceutical composition or a dosage form depends on various factors well known in the art, including methods of formulating preparations to be administered to a patient, but is not limited thereto. For example, dosage forms for oral administration such as tablets can include an excipient not suitable for use in preparations for non-oral administration.

The pharmaceutical compositions include those suitable for aerosol, pulmonary, inhalation, oral, parenteral (including subcutaneous, intradermal, intramuscular, intravenous and intraarticular), rectal and topical (including dermal, buccal, sublingual and intraocular) administration. The most suitable route can depend upon the condition and disorder of the recipient. The compositions can conveniently be presented in unit dosage form and can be prepared by any of the methods well known in the art of pharmacy. In general, the compositions are prepared by uniformly and intimately bringing into association the active ingredient with liquid carriers or finely divided solid carriers or both and then, if necessary, shaping the product into the desired composition.

Compositions of the present disclosure can also optionally include other therapeutic ingredients, anti-caking agents, preservatives, sweetening agents, colorants, flavors, desiccants, plasticizers, dyes, and the like. Any such optional ingredient must, of course, be compatible with the compound of the disclosure to insure the stability of the composition.

The active agents, alone or in combination with other suitable components, can be administered by pulmonary route utilizing several techniques including but not limited to intratracheal instillation (delivery of solution into the lungs by syringe), intratracheal delivery of liposomes, insufflation (administration of powder composition by syringe or any other similar device into the lungs) and aerosol inhalation. Compositions suitable for pulmonary route inhalation include sterile solutions for nebulization comprising a therapeutically effective amount of the compound dissolved in aqueous saline solution and optionally containing a preservative such as benzalkonium chloride or chlorobutanol, and aerosol compositions comprising a therapeutically effective amount dissolved or suspended in an appropriate propellant. Aerosols (e.g., jet or ultrasonic nebulizers, metered-dose inhalers (MDIs), and dry-powder inhalers (DPIs)) can also be used in intranasal applications. Aerosols can be conveniently presented in unit dosage form and prepared by any of the methods well-known in the art of pharmacy. Aerosol compositions are stable dispersions or suspensions of solid material and liquid droplets in a gaseous medium and can be placed into pressurized acceptable propellants, such as hydrofluoroalkanes (HFAs, i.e., HFA-134a and HFA-227, or a mixture thereof), dichlorodifluoromethane (or other chlorofluocarbon propellants such as a mixture of Propellants 11, 12, and/or 114), propane, nitrogen, and the like. Pulmonary compositions can include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion. Pulmonary compositions can also include surfactants, which include but are not limited to bile salts and those described in U.S. Pat. No. 6,524,557 and references therein. The surfactants described in U.S. Pat. No. 6,524,557, e.g., a C8-C16 fatty acid salt, a bile salt, a phospholipid, or alkyl saccharide are advantageous in that some of them also reportedly enhance absorption of the compound in the composition.

Also suitable are dry powder compositions comprising a therapeutically effective amount of active compound blended with an appropriate carrier and adapted for use in connection with a dry-powder inhaler. Absorption enhancers which can be added to dry powder compositions of the present disclosure include those described in U.S. Pat. No. 6,632,456. WO02/080884 describes new methods for the surface modification of powders. Aerosol compositions can include U.S. Pat. Nos. 5,230,884, 5,292,499, WO017/8694, WO01/78696, US2003019437, US20030165436, and WO96/40089 (which includes vegetable oil). Sustained release compositions suitable for inhalation are described in US20010036481A1, US20030232019A1, and US20040018243A1 as well as in WO01/13891, WO02/067902, WO03/072080, and WO03/079885. Pulmonary compositions containing microparticles are described in WO03/015750, US20030008013, and WO00/00176. Pulmonary compositions containing stable glassy state powder are described in US20020141945 and U.S. Pat. No. 6,309,671. Other aerosol compositions are described in EP 1338272A1, WO90/09781, U.S. Pat. Nos. 5,348,730, 6,436,367, WO91/04011, and U.S. Pat. Nos. 6,294,153 and 6,290,987 describes a liposomal based composition that can be administered via aerosol or other means. Powder compositions for inhalation are described in US20030053960 and WO01/60341. The agents can be administered intranasally as described in US20010038824.

While the pulmonary route is advantageous in most instances, there can also be instances in which other routes of administration can be advantageous. For example, oral administration can be desirable. In that regard, one can contemplate administration using a composition in which the compound is releasably encapsulated by modified amino acids, as described in U.S. Pat. No. 5,811,127. One can also contemplate administration as an implantable sustained-release dosage form, such as described in US20040115236.

The pharmaceutical compositions containing the active ingredient can be in a form suitable for oral use, for example, as tablets, troches, lozenges, aqueous or oily suspensions, dispersible powders or granules, emulsions, hard or soft capsules, or syrups or elixirs. Compositions intended for oral use can be prepared according to any method known to the art for the manufacture of pharmaceutical compositions. Such compositions can contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. They can also be coated by the techniques described in U.S. Pat. Nos. 4,256,108; 4,160,452; and 4,265,874 to form osmotic therapeutic tablets for control release.

A tablet can be made by compression or molding, optionally with one or more accessory ingredients. Compressed tablets can be prepared by compressing in a suitable machine the active ingredient in a free-flowing form such as a powder or granules, optionally mixed with a binder, lubricant, inert diluent, lubricating, surface active or dispersing agent. Molded tablets can be made by molding in a suitable machine a mixture of the powdered compound moistened with an inert liquid diluent. The tablets can optionally be coated or scored and can be formulated so as to provide sustained, delayed or controlled release of the active ingredient therein.

Compositions for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropyl-methylcellulose, sodium alginate, polyvinyl-pyrrolidone, gum tragacanth and gum acacia; dispersing or wetting agents can be a naturally-occurring phosphatide, for example lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example, ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, can also be present.

The pharmaceutical compositions can be in the form of a sterile injectable aqueous or oleagenous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, for example as a solution in 1,3-butane diol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

The pharmaceutical compositions and methods of the disclosure can further comprise other therapeutically active compounds, as noted herein, useful in the treatment of asthma, allergic diseases, and inflammatory conditions. In many instances, compositions which include a compound disclosed herein and an alternative agent have additive or synergistic effects when administered.

The pharmaceutical compositions for the administration of the compounds of this disclosure can conveniently be presented in unit dosage form and can be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired composition. In the pharmaceutical composition the active object compound is included in an amount sufficient to produce the desired effect upon the process or condition of diseases.

Methods of Use

The term "subject" or "patient" is defined herein to include animals such as mammals, including, but not limited to, primates (e.g., human or nonhuman), cows, sheep, goats, horses, dogs, cats, rabbits, rats, mice and the like. In some embodiments, the subject is a human.

The terms "prevent", "preventing" and "prevention", as used herein, refer to a method of delaying or precluding the onset of a disease and/or its attendant symptoms, barring a subject from acquiring a disease or reducing a subject's risk of acquiring a disease.

The terms "treat", "treating" and "treatment", as used herein, are meant to include alleviating, reducing, or abrogating a disease or condition and/or its attendant symptoms and alleviating, reducing, or eradicating the cause of the disease itself.

The term "therapeutically effective amount" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

Disclosed herein are methods of treating asthma in a subject in need thereof, the method comprising administering to the subject a pharmaceutical composition comprising a compound represented by Formula 1 or a pharmaceutically acceptable salt thereof and a pharmaceutically acceptable excipient:

[Formula 1]

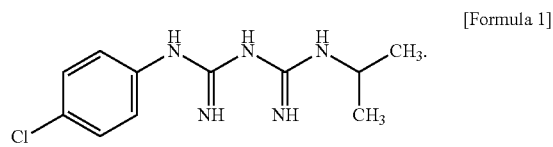

Also disclosed herein are methods of treating asthma in a subject in need thereof, the methods comprising administering to the subject a pharmaceutical composition comprising a compound represented by Formula 1 or a pharmaceutically acceptable salt thereof, a compound represented by Formula 2 or a pharmaceutically acceptable salt thereof, and a pharmaceutically acceptable excipient:

[Formula 1]

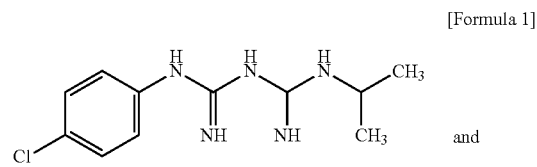

and

[Formula 2]

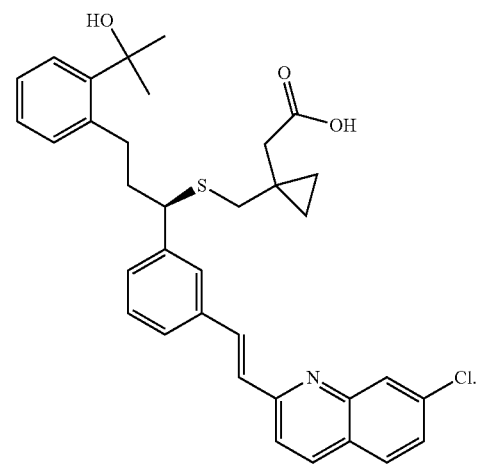

Also disclosed are methods of treating asthma in a subject in need thereof, the methods comprising administering to the subject a pharmaceutical composition comprising proguanil and other anti-asthma agents, such as zileuton, zafirlukast, terbutaline sulfate, and albuterol. Methods for preventing and/or treating asthma includes allergen-induced asthma, viral-induced asthma, cold-induced asthma, pollution-induced asthma and/or exercise-induced asthma.

In some embodiments of the methods of treating asthma, the compositions are administered orally to the subject. In some embodiments of the methods of treating asthma, the compositions comprise 0.001 mg to 100 mg of each of the compound per kg of the subject's body weight.

Also disclosed herein are methods of treating Parkinson's disease in a subject in need thereof, the methods comprising administering to the subject a pharmaceutical composition comprising a compound represented by Formula 1 or a pharmaceutically acceptable salt thereof and a pharmaceutically acceptable excipient:

[Formula 1]

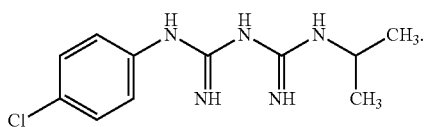

Also disclosed herein are methods of treating Parkinson's disease in a subject in need thereof, the methods comprising administering to the subject a pharmaceutical composition comprising a compound represented by Formula 1 or a pharmaceutically acceptable salt thereof, a compound represented by Formula 2 or a pharmaceutically acceptable salt thereof, and a pharmaceutically acceptable excipient:

[Formula 1]

[Formula 2]

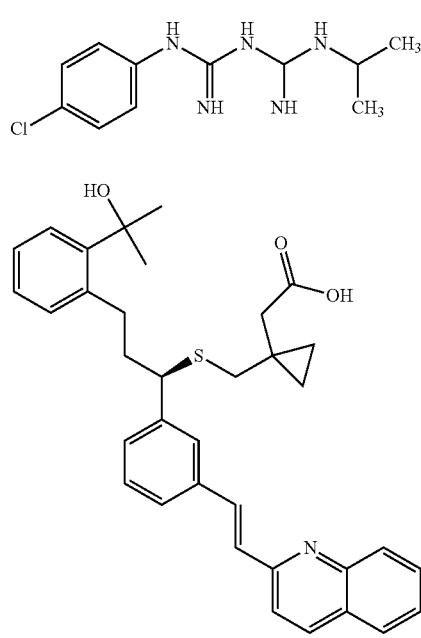

In some embodiments of the methods of treating Parkinson's disease, the compositions are administered orally to the subject. In some embodiments of the methods of treating Parkinson's disease, the compositions comprise 0.001 mg to 100 mg of each of the compound per kg of the subject's body weight.

Depending on the disease to be treated and the subject's condition, the compounds of the disclosure can be administered by aerosol, pulmonary, inhalation, oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and can be formulated, alone or together, in suitable dosage unit compositions containing conventional non-toxic pharmaceutically acceptable carriers, adjuvants and vehicles appropriate for each route of administration. The disclosure also contemplates administration of the compounds of the disclosure in a depot composition, in which the active ingredient is released over a defined time period.

The dose range of the active ingredient(s) or a pharmaceutically acceptable salt thereof for adult humans is generally from about 0.005 mg/day to about 10 g/day, from about 1 mg/day to about 1,000 mg/day, about 10 mg/day to about 750 m/day, about 50 mg/day to about 500 mg/day, or about 75 mg/day to about 350 mg/day. Tablets or other forms of presentation provided in discrete units can conveniently contain an amount of compound of the disclosure which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

In the treatment or prevention of asthma, an appropriate dosage level will generally be about 0.001 to 100 mg per kg patient body weight per day, which can be administered in single or multiple doses. The dosage level can be about 0.01 mg/kg per day to about 75 mg/kg per day or about 0.05 mg/kg per day to about 20 mg/kg per day. A suitable dosage level can be about 0.01 mg/kg per day to about 50 mg/kg per day, about 0.05 mg/kg per day to about 20 mg/kg per day, or about 0.1 mg/kg per day to about 10 mg/kg per day. Within this range the dosage can be 0.01 mg/kg per day to 0.1 mg/kg per day, 0.1 mg/kg per day to 1 mg/kg per day, 1 mg/kg per day to 10 mg/kg per day. For oral administration, the compositions can be provided in the form of tablets containing 1 mg to 1000 mg of the active ingredient, such as but not limited to 1 mg, 5 mg, 10 mg, 15 mg, 20 mg, 25 mg, 50 mg, 75 mg, 100 mg, 150 mg, 200 mg, 250 mg, 300 mg, 400 mg, 500 mg, 600 mg, 750 mg, 800 mg, 900 mg, and 1000 mg of the active ingredient for the symptomatic adjustment of the dosage to the patient to be treated. The compounds can be administered on a regimen of 1 to 4 times per day, e.g., once, twice, thrice, or four times per day.

Similarly, in the treatment or prevention of Parkinson's disease, an appropriate dosage level will generally be about 0.001 to 100 mg per kg patient body weight per day, which can be administered in single or multiple doses. The dosage level can be about 0.01 mg/kg per day to about 75 mg/kg per day or about 0.05 mg/kg per day to about 20 mg/kg per day. A suitable dosage level can be about 0.01 mg/kg per day to about 50 mg/kg per day, about 0.05 mg/kg per day to about 20 mg/kg per day, or about 0.1 mg/kg per day to about 10 mg/kg per day. Within this range the dosage can be 0.01 mg/kg per day to 0.1 mg/kg per day, 0.1 mg/kg per day to 1 mg/kg per day, 1 mg/kg per day to 10 mg/kg per day. For oral administration, the compositions can be provided in the form of tablets containing 1 mg to 1000 mg of the active ingredient, such as but not limited to 1 mg, 5 mg, 10 mg, 15 mg, 20 mg, 25 mg, 50 mg, 75 mg, 100 mg, 150 mg, 200 mg, 250 mg, 300 mg, 400 mg, 500 mg, 600 mg, 750 mg, 800 mg, 900 mg, and 1000 mg of the active ingredient for the symptomatic adjustment of the dosage to the patient to be treated. The compounds can be administered on a regimen of 1 to 4 times per day, e.g., once, twice, thrice, or four times per day.

In some embodiments, the dosage of proguanil or montelukast is provided at about 0.05 mg/day to about 1000 mg/day, including any and all variations within this range, such as about 0.1 mg/day to about 1000 mg/day, about 1 mg/day to about 1000 mg/day, about 2.5 mg/day to about 100 mg/day, about 5 mg/day to about 50 mg/day, about 10 mg/day to about 750 mg/day, about 50 mg/day to about 500 mg/day, or about 75 mg/day to about 350 mg/day.

In some embodiments, montelukast is provided as a tablet, a chewable tablet, and granules to be taken by mouth. Montelukast can be taken once a day with or without food. Montelukast can be administered as montelukast sodium, with 5.2 mg of montelukast sodium being equivalent to 5 mg of montelukast.

It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present disclosure can be combined or used in combination with other agents useful in the treatment, prevention, suppression or amelioration of the diseases or conditions for which compounds of the disclosure are useful.

Such other agents, or drugs, can be administered, by a route and in an amount commonly used therefor, simultaneously or sequentially with a compound of the disclosure. When a compound of the disclosure is used contemporaneously with one or more other drugs, a pharmaceutical composition containing such other drugs in addition to the compound of the disclosure is preferred. Accordingly, the pharmaceutical compositions of the disclosure include those that also contain one or more other active ingredients or therapeutic agents, in addition to a compound of the disclosure.

The weight ratio of the compound of the disclosure to the second active ingredient can be varied and will depend upon the effective dose of each ingredient. Generally, an effective dose of each will be used. Thus, for example, when a compound of the disclosure is combined with an NSAID, the weight ratio of the compound of the disclosure to the NSAID will generally range from about 1000:1 to about 1:1000, or about 200:1 to about 1:200. Combinations of a compound of the disclosure and other active ingredients will generally also be within the aforementioned range, but in each case, an effective dose of each active ingredient should be used.

Hereinafter, the present disclosure will be described in further detail with reference to the following non-limiting examples. However, these examples are provided for illustrative purposes only and are not intended to limit the scope of the present disclosure.

EXAMPLES

Example 1. In Vitro Cell Viability Assay (MTT)

IPS-07004 (proguanil) was purchased from Key Organics (London, UK).

A549 lung carcinoma cells ($1\times10^3$/well) were seeded on a 96-well plate for 16 hrs. After starvation for 24 hrs., the cells were pretreated with LPS or IL-1b for 4 hrs. The cells were then treated with IPS-07004 for 24 hrs. in a dose-dependent manner. After 48 hrs. of incubation, MTT [3-(4,5-dimethylthiazol-2-yl)-2,5-diphenyl-tetrazolium bromide] solution (5 mg/ml) was added to each well in an amount of 1/10 of total volume, and the cells were incubated for 2 hrs. at 37° C.

To examine the survival rate for A549 cells treated with IPS-07004, an in vitro cell viability assay was performed using MTT. There were little or no effect of IPS-07004 on the viability when the cells were induced by LPS (lipopolysaccharide) and IL-1beta (interleukin-1beta) (FIG. 1).

Example 2. Enzyme-Linked Immunosorbent Assay (ELISA) of IL-6 and IL-8

A549 cells ($1\times10^5$/well) were seeded on a 96-well plate for 16 hrs. After starvation for 24 hrs., the cells were pretreated with LPS or IL-1beta for 4 hrs. The cells were then treated with IPS-07004 for 24 hrs. in a dose-dependent manner. Cytokines levels (IL-6 and IL-8) in media were analyzed in accordance with the manufacturer's specification (BD Biosciences Pharmingen, San Diego, Calif., USA).

To assess whether IPS-07004 inhibits the expression of IL-6 and IL-8, which play a critical role in asthma pathology, ELISA of the cytokines in A549 cells was employed.

Figure 2:
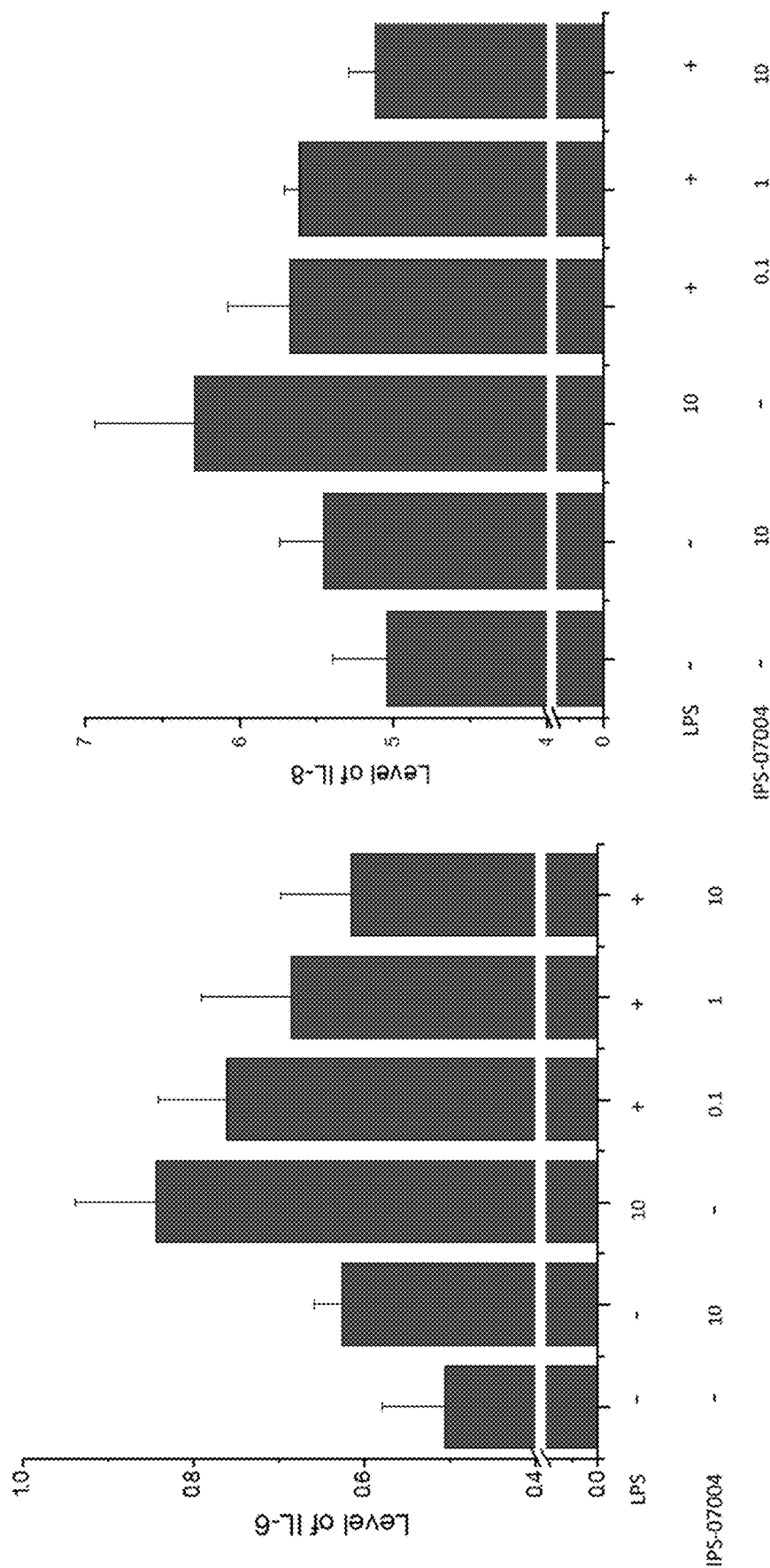
FIG. 2. Effect of IPS-07004 on the expression of IL-6 and IL-8 in A549 lung carcinoma cells induced by LPS.
Figure 3:
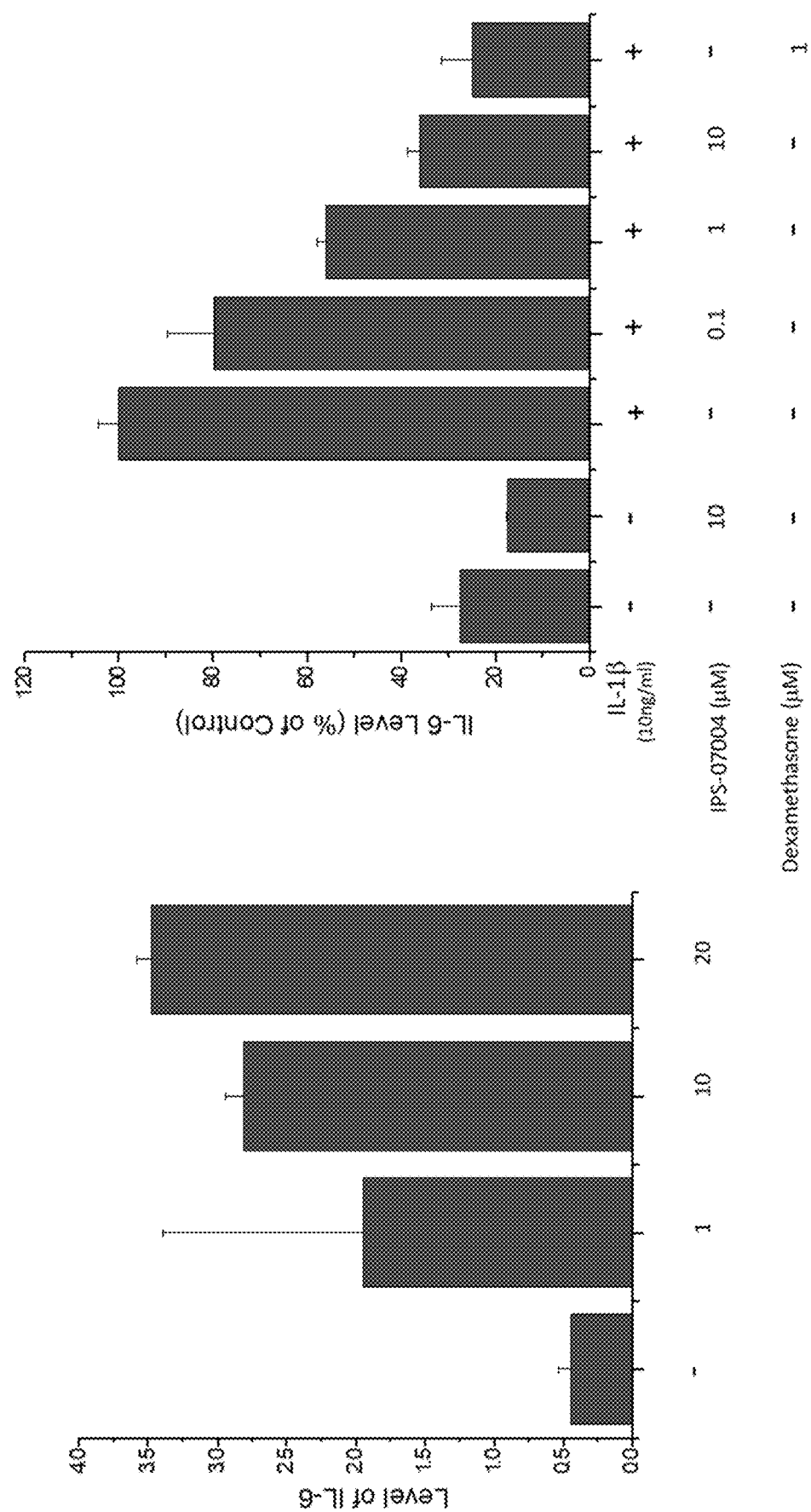
FIG. 3. Effect of IPS-07004 on the expression of IL-6 in A549 lung carcinoma cells induced by IL-1 beta.
Figure 4:
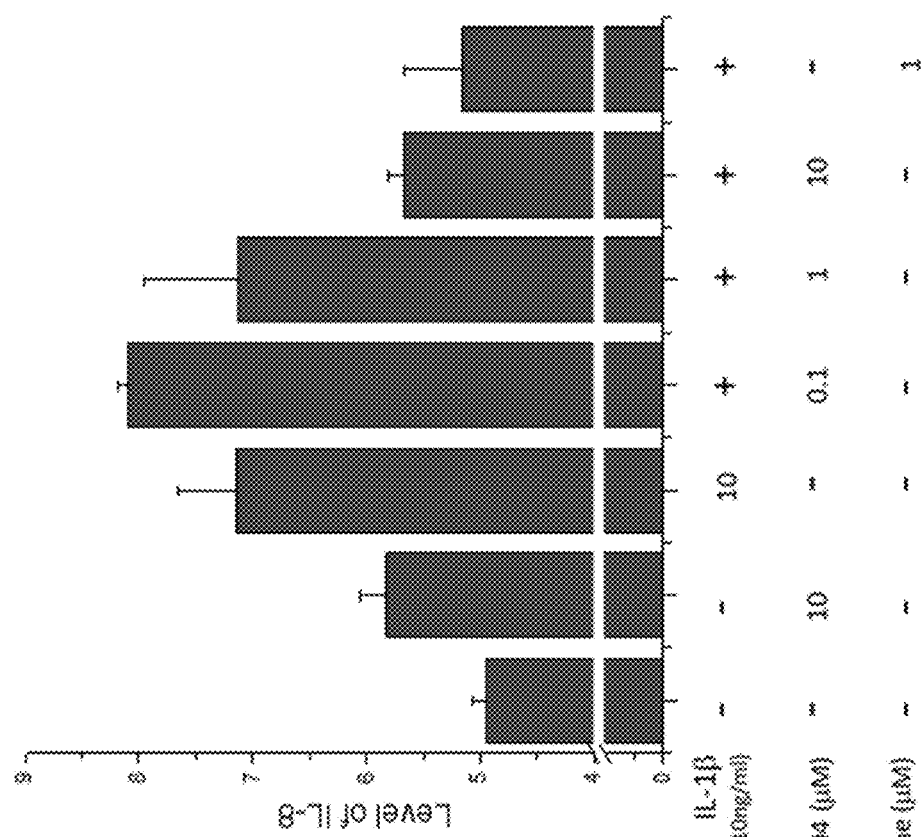
FIG. 4. Effect of IPS-07004 on the expression of IL-8 in A549 lung carcinoma cells induced by IL-1 beta.
Figure 4:
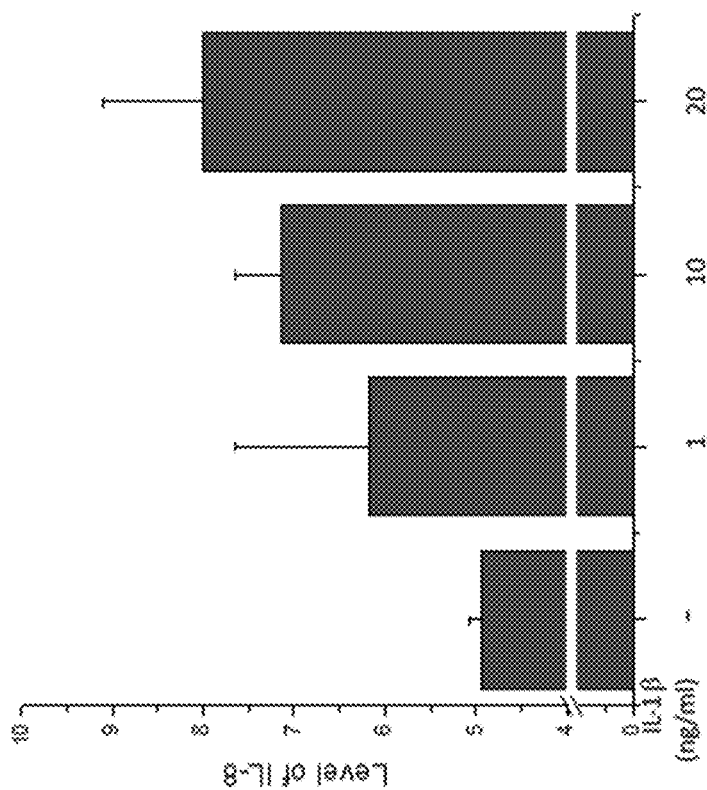

IPS-07004 reduced the expression levels of IL-6 and IL-8 in A549 cells induced by LPS (FIG. 2) and IL-1beta (FIGS. 3 and 4) in a dose-dependent manner. These data indicate that IPS-07004 is applicable for treating asthma.

Example 3. Effect of the Combined Treatment of IPS-07004 and Montelukast on the Expression of IL-6 and IL-8 in A549 Lung Carcinoma Cells Induced by LPS or IL-1beta To examine the synergistic effect of IPS-07004 combined with Motelukast (an anti-asthma agent) on the anti-asthmatic function, cytokine expression assay in A549 cells was carried out.

Figure 5:
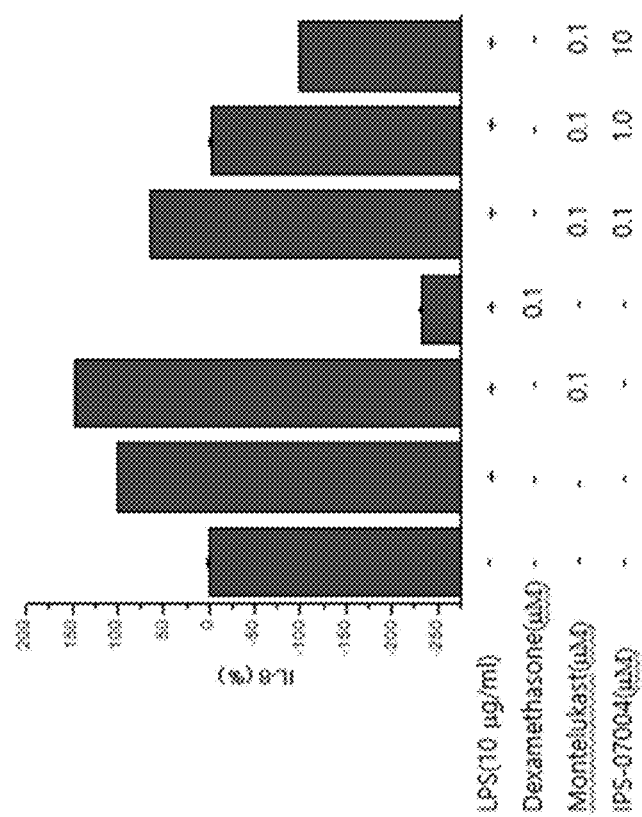
FIG. 5. Effect of the combined treatment of IPS-07004 and Montelukast on the expression of IL-6 and IL-8 in A549 lung carcinoma cells induced by LPS.
Figure 5:
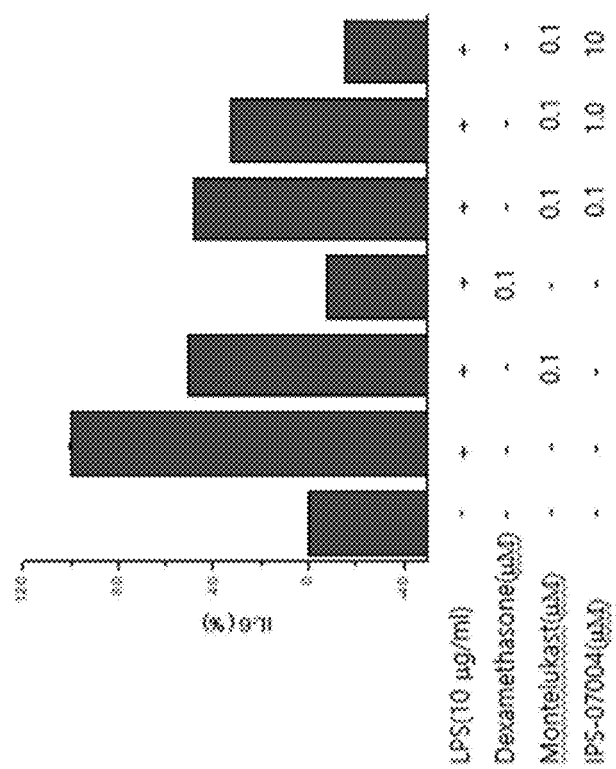
Figure 6:
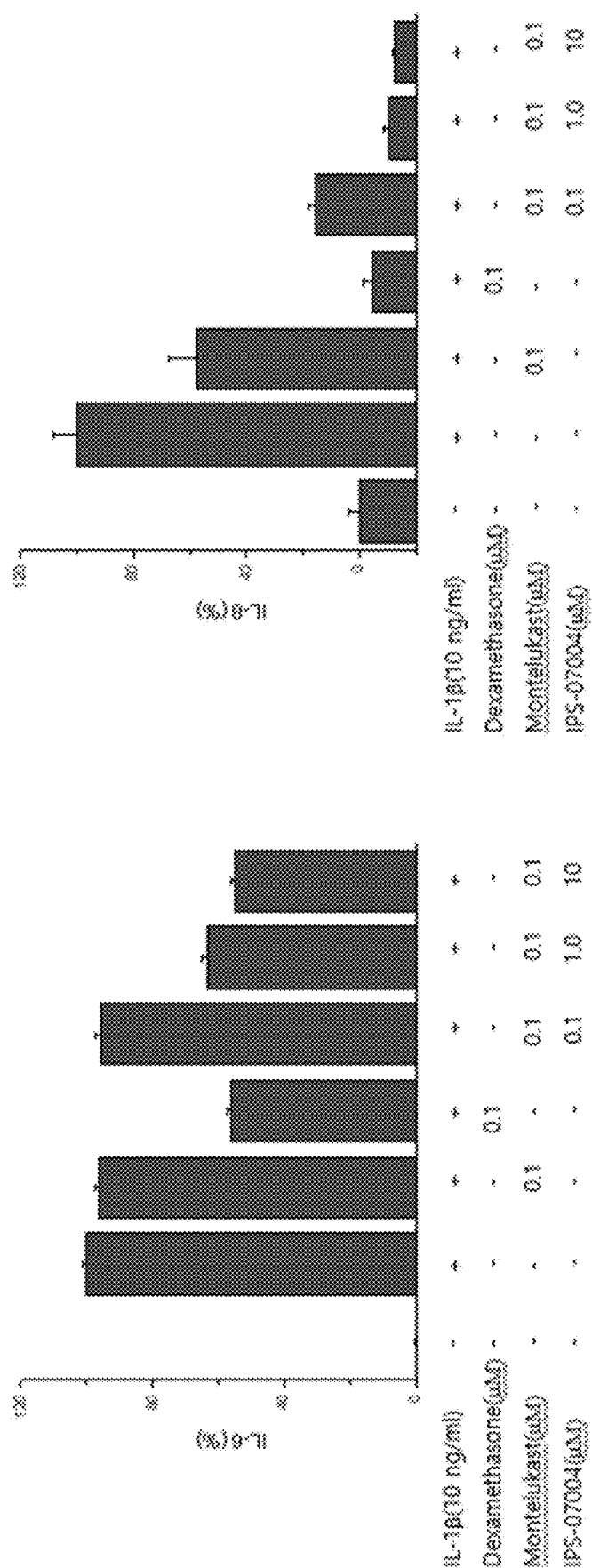
FIG. 6. Effect of the combined treatment of IPS-07004 and Montelukast on the expression of IL-6 and IL-8 in A549 lung carcinoma cells induced by IL-1beta.

The combination of IPS-07004 with Montelukast appeared to be more effective in suppressing the expression of IL-6 and IL-8 in A549 cells induced by LPS (FIG. 5) and IL-1beta (FIG. 6) compared with treatment with Motelukast alone. These data indicate that IPS-07004 can be used for combined therapy with Montelukast for treating asthma.

Example 4. Compound Profile of IPS-07005

Figure 7:
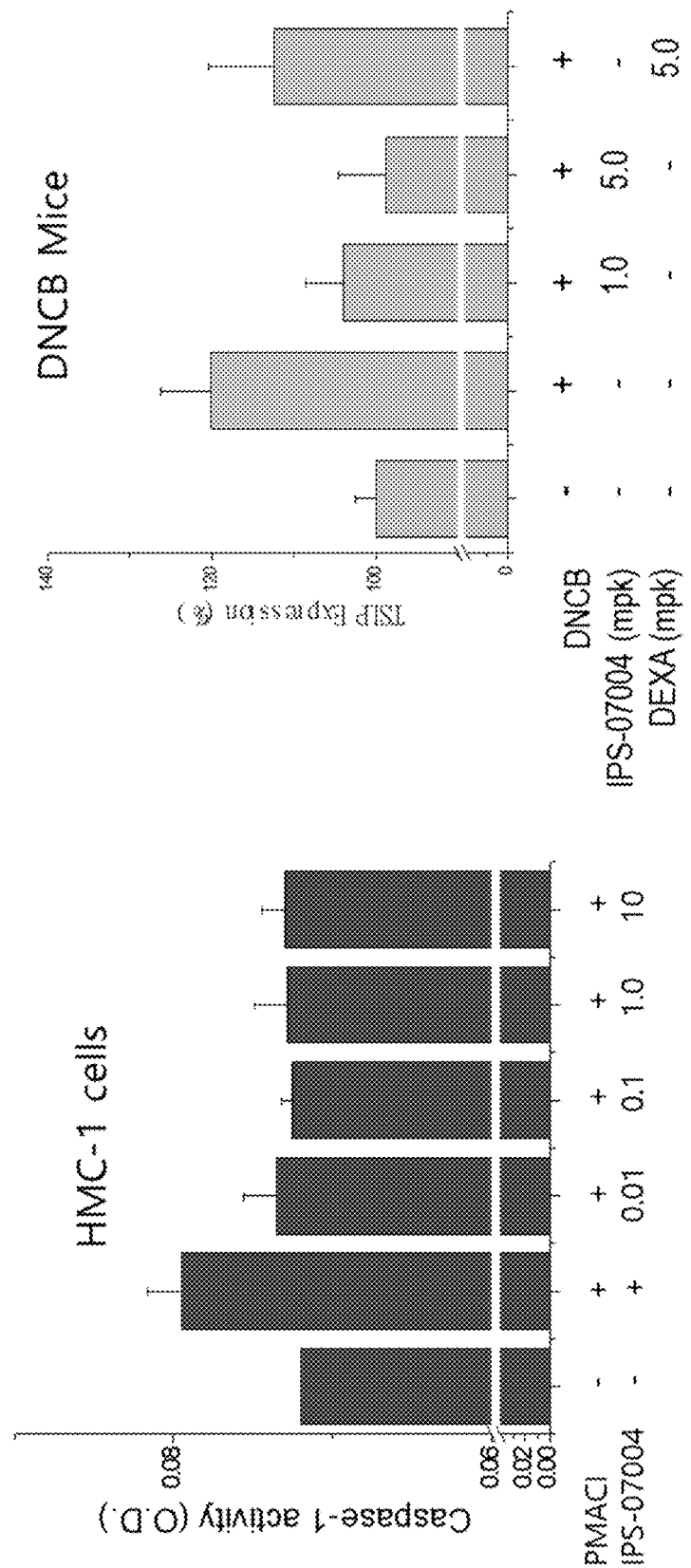
FIG. 7. Inhibitory effect of IPS-07004 on TSLP expression in mice and HMC-1 cells.
Figure 8:
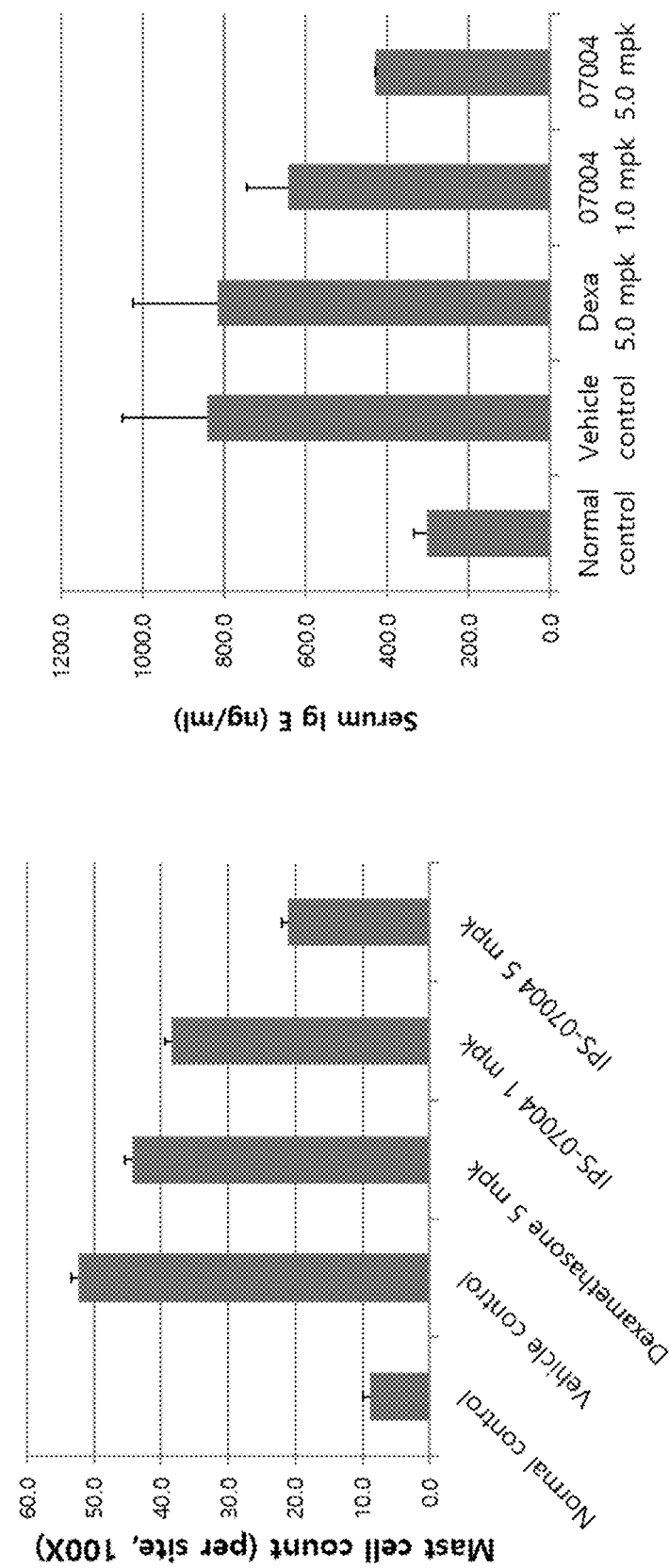
FIG. 8. Inhibitory effect of IPS-07004 on mast cell number and serum IgE level.

Indication: Asthma
Mode of action target: NLRP3 inflammasome-derived Caspase-1 inhibitor
Lead material: IPS-07004
Composition: IPS-07004 10 mg/kg (mpk)+Montelukast 1.0 mpk
Development step: Phase I
FIG. 7 shows the inhibitory effect of IPS-07004 on Caspase-1 activity and TSLP (Thymic Stromal Lymphopoietin) expression in HMC-1 cells and DNCB (2,4-dinitrochlorobenzene) mice.
FIG. 8 shows the inhibitory effect of IPS-07004 on mast cell number and serum IgE level.

Example 5. Inhibitory Effect of IPS-07005 on Asthma—In Vitro Cell-Based Assay

Results

Figure 9:
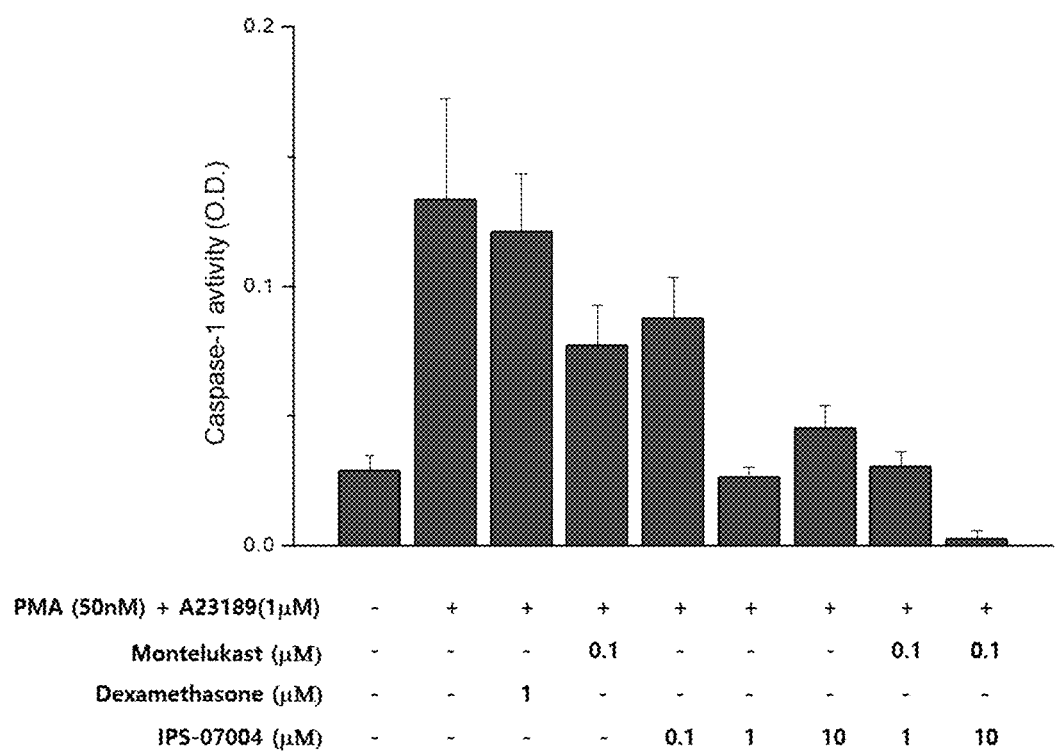
FIG. 9. Effect of IPS-07005 on human Caspase-1 activity in HMC-1 cells.

Using HMC-1 (human mast cell line) cell-based assay, IPS-07005 ((IPS-07004+Montelukast) inhibited the activity of Caspase-1, a critical component of inflammasome, to suppress the conversion of Pro-TSLP, IL-1beta, and -IL-18 to active forms as shown in FIG. 9.

IPS-07004 alone inhibited caspase-1 activity in HMC-1 cells in a dose-dependent manner and IPS-07005 provided a synergistic effect.

Figures 10A, 10B:
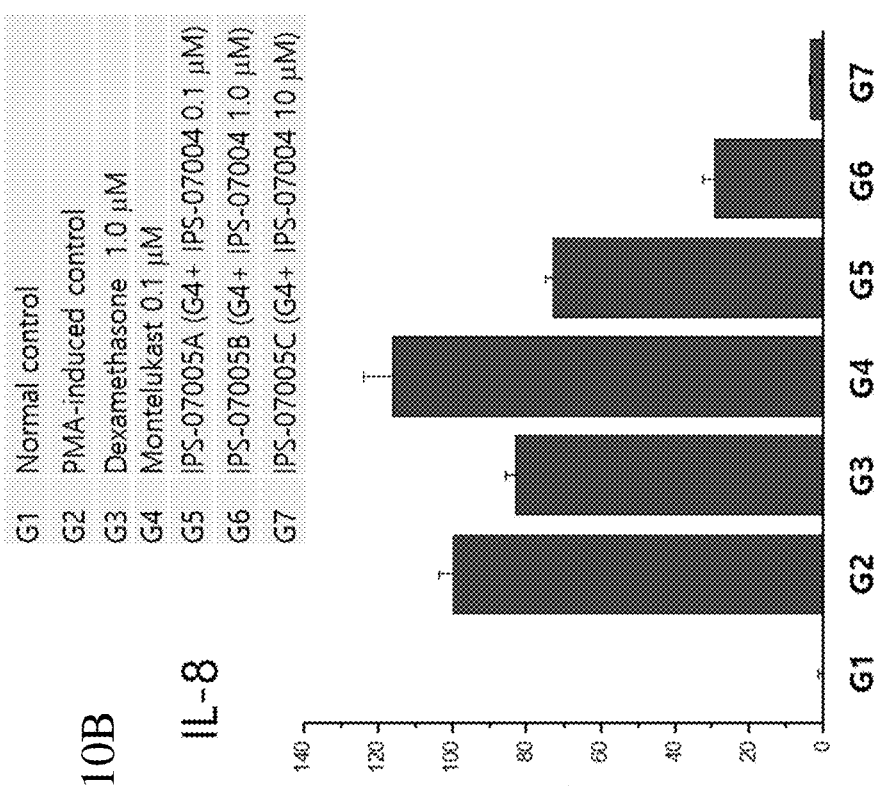
FIGS. 10A and 10B. Effect of IPS-07005 on the expression on IL-6 and IL-8 in HMC-1 cells induced by PMA.

FIG. 10 shows the effect of IPS-07005 on the expression of IL-6 and IL-8 in HMC-1 cells induced by PMA (Phorbol 12-myristate 13-acetate) and A23187, a calcium ionophore (C1). IPS-07005 inhibited the expressions of IL-6 and IL-8 compared with IPS-07004, montelukast alone or dexamethasone in HMC-1 cells.

Figure 11B:
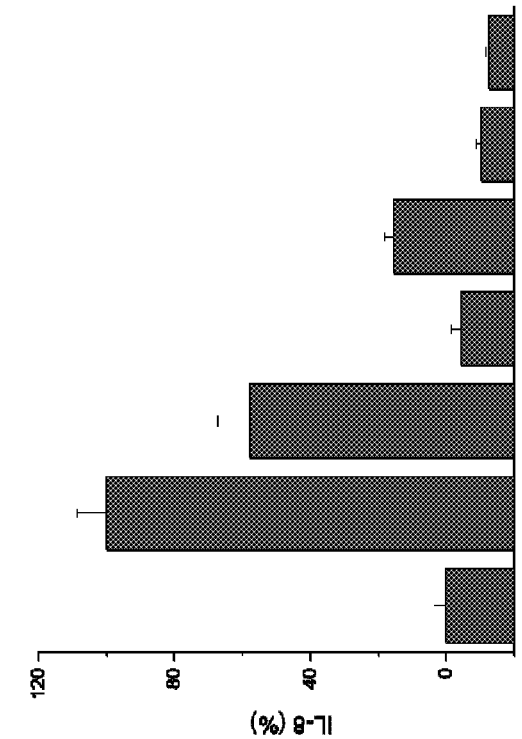
FIGS. 11A and 11B. Effect of the combined treatment of IPS-07005 on the expression of IL-6 and IL-8 in A549 lung carcinoma cells induced by IL-1$\beta$.
Figure 11A:
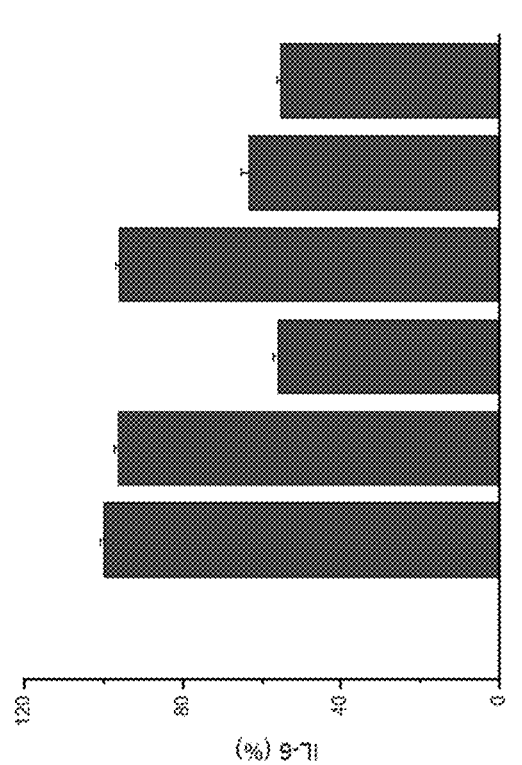

To assess whether IPS-07005 inhibits the expression of IL-6 and IL-8 which play a critical role in asthma pathology, ELISA of the cytokines in A549 lung carcinoma cells was employed. IPS-07005 reduced the expression levels of IL-6 and IL-8 in A549 cells induced by IL-1β (FIG. 11) in a dose-dependent manner. IPS-07005 inhibited the expression of IL-6 and IL-8 compared to IPS-07004, montelukast alone, or dexamethasone in A549 cells (human lung cancer cells).

These data indicate that IPS-07005 is applicable for treating asthma.

Example 6. Inhibitory Effect of IPS-07005 on Asthma—In Vivo Animal Data

Figure 12:
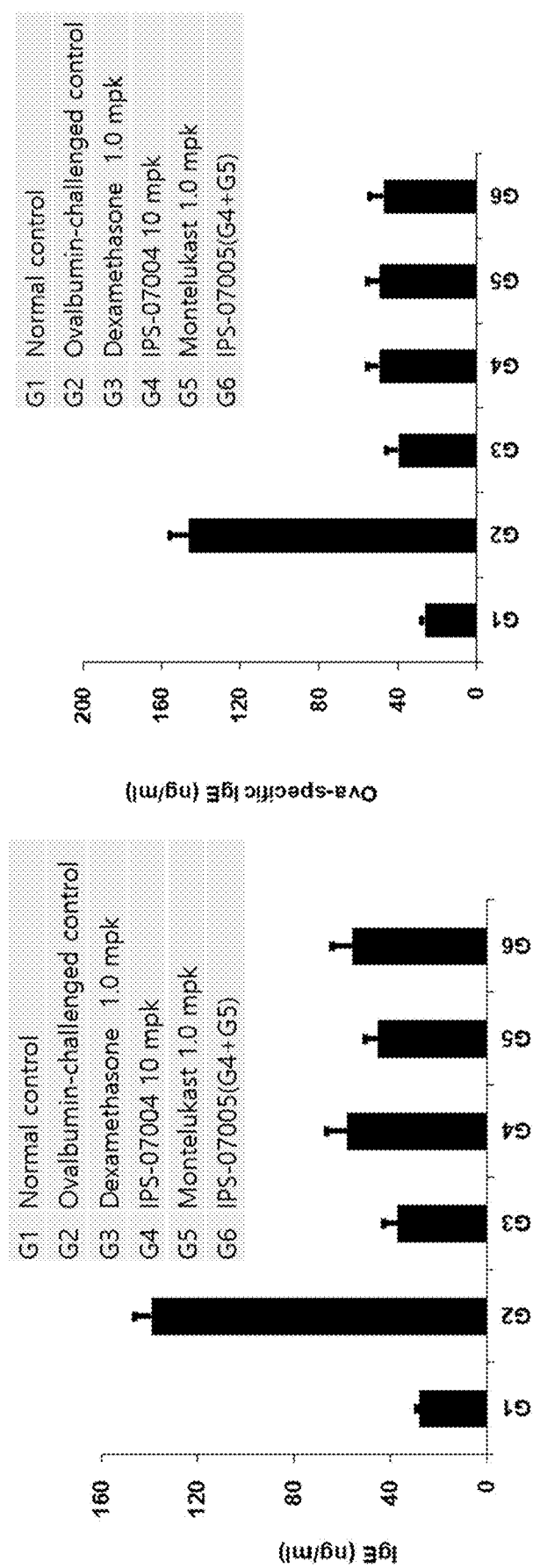
FIG. 12. Inhibitory effect of IPS-07005 on OVA-specific IgE expression.

FIG. 12 shows the inhibitory effect of IPS-07005 on OVA-specific IgE expression. IPS-07005 (IPS-07004 10 mpk+montelukast 1 mpk) showed significant reduction of OVA-induced IgE level in bronchoalveolar lavage fluid (BALF).

Figure 13A:
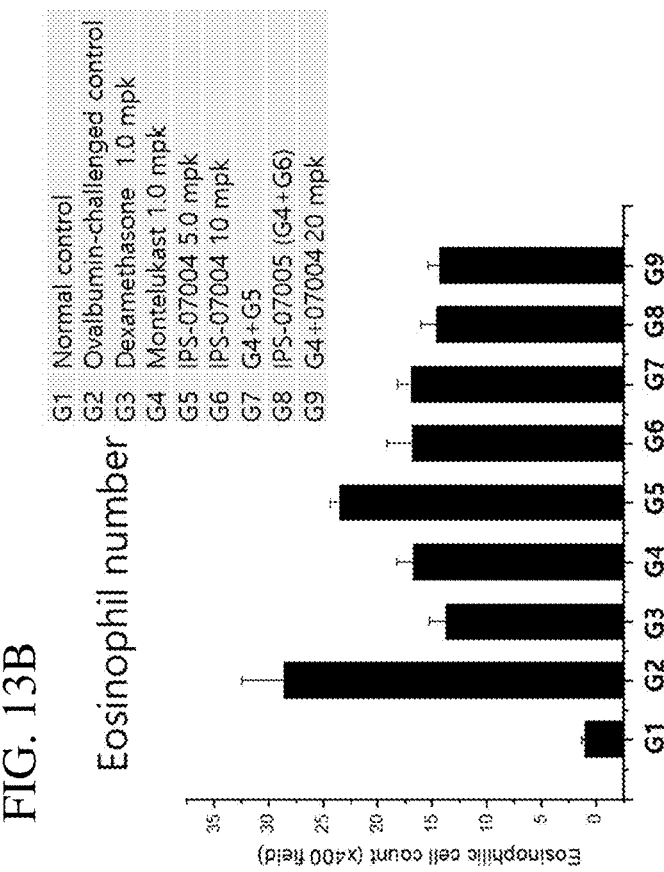
FIGS. 13A and 13B. Inhibitory effect of IPS-07005 on total cell number and eosinophil number in bronchoalveolar lavage (BAL) fluid.
Figure 13B:
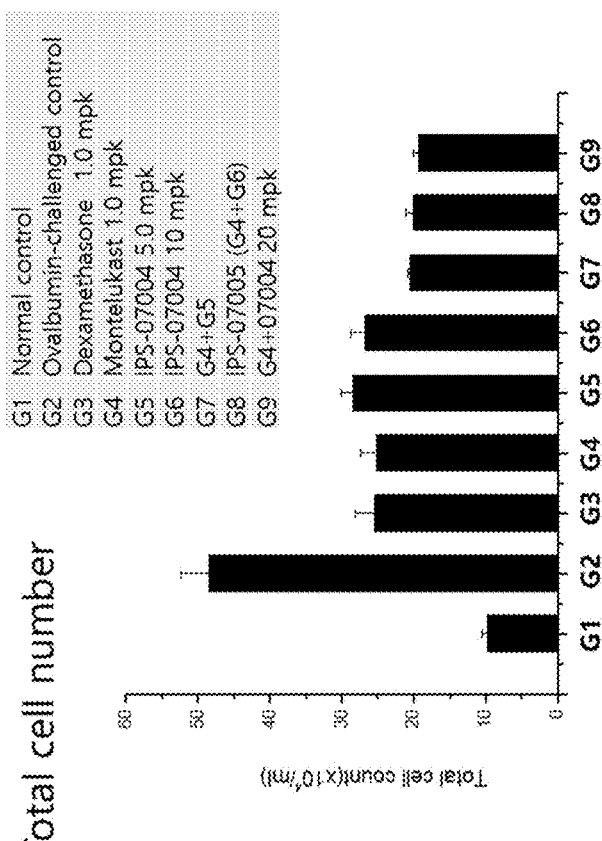
Figure 13C:
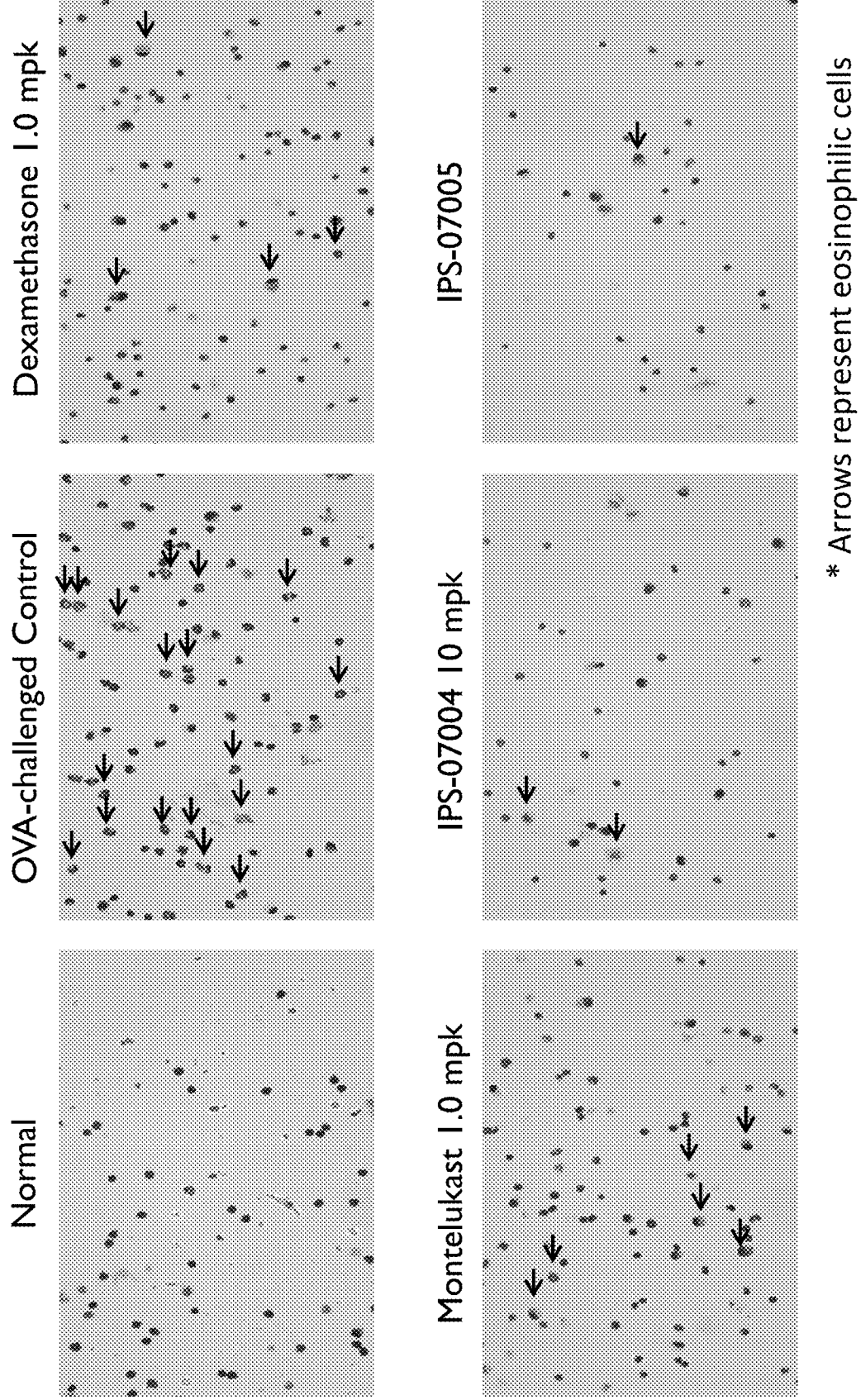
FIG. 13C. Histological images of eosinophils.

FIGS. 13A and 13B show the inhibitory effect of IPS-07005 on total cell number and eosinophil number in bronchoalveolar lavage (BAL) fluid. FIG. 13C shows decreased number of eosinophils in OVA-challenged cells when treated with IPS-07004 or IPS-07005. Analysis of the inflammatory cells in the BALF samples revealed that total cell numbers were significantly increased by OVA sensitization. However, total cell numbers were reduced by treatment with IPS-07005. Specifically, administration of IPS-07005 also significantly reduced the total and eosinophil cell counts in BALF in the corresponding group compared with the OVA-challenged group (FIGS. 13A and 13B).

Figure 14:
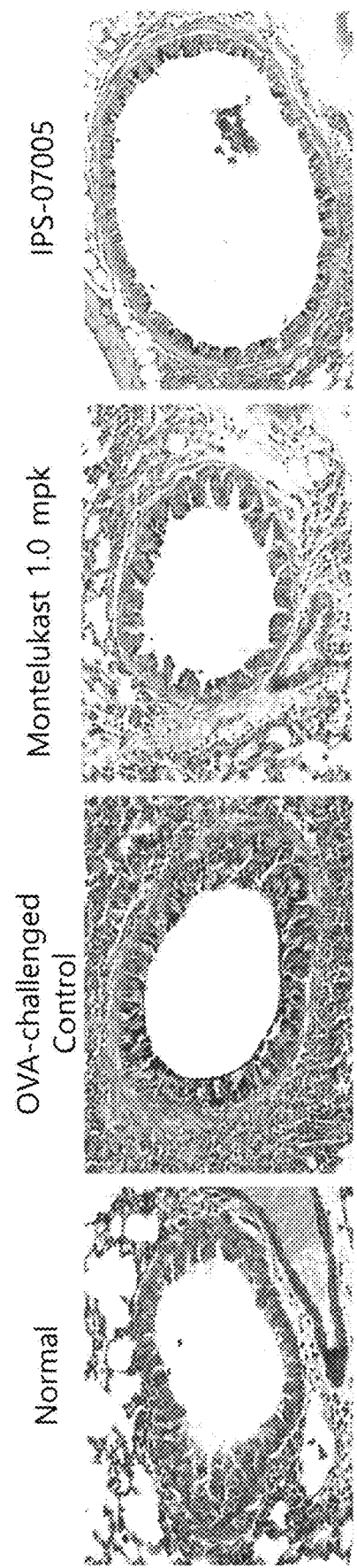
FIG. 14. Effect of IPS-07005 on OVA-induced lung histological changes, as determined by H&E staining (100×).
Figure 15A:
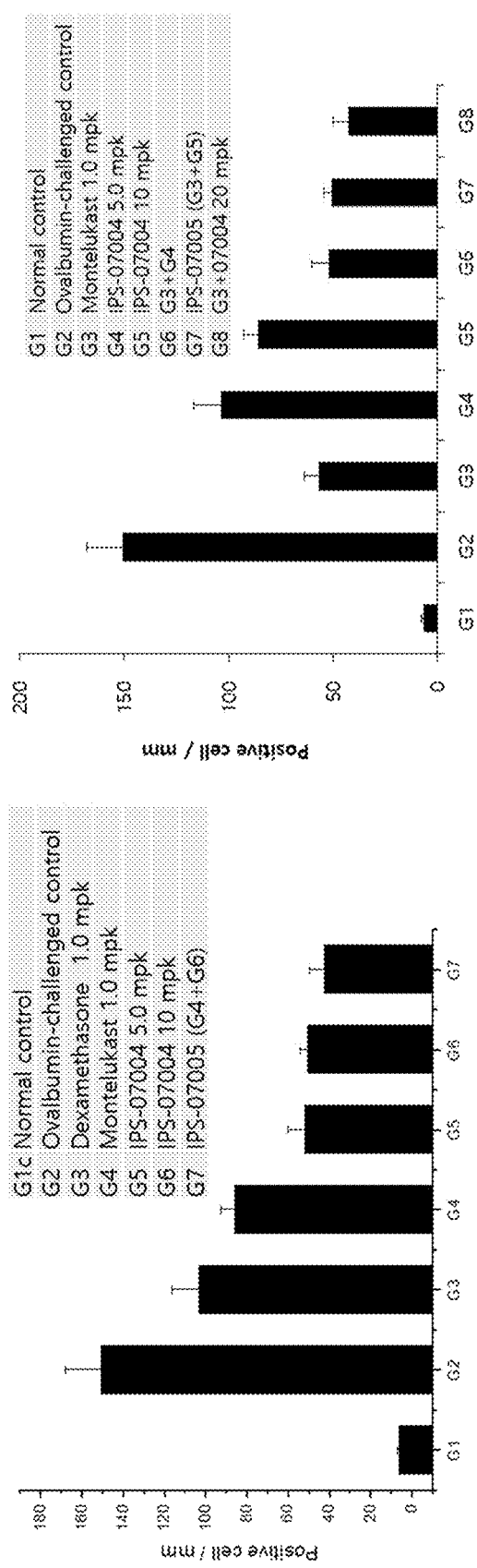
FIGS. 15A and 15B. Histological images of airways stained with PAS for goblet cell visualization.
Figure 15B:
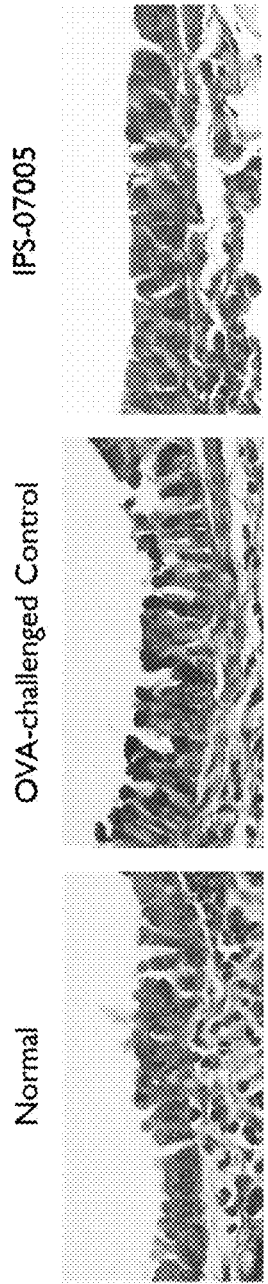

FIG. 14 shows the effects of IPS-07005 on OVA-induced lung histological changes, as determined by H&E staining (100×). FIG. 14 shows the histological images of airways stained with PAS for goblet cell visualization. The lung sections were stained with PAS (Periodic acid-Schiff) to evaluate their levels of goblet cell hyperplasia. We observed noticeable differences in the sizes of the purple areas, i.e., the areas of lung tissue stained with PAS, among the three groups. We noted goblet cell hyperplasia and mucus overproduction in the bronchial passages of OVA-challenged mice. However, we noted a significantly lower number of goblet cells in the IPS-07005 and high dose of Montelukast-treated groups than in the OVA-challenged group (FIGS. 15A and 15B).

Figures 16A, 16B:
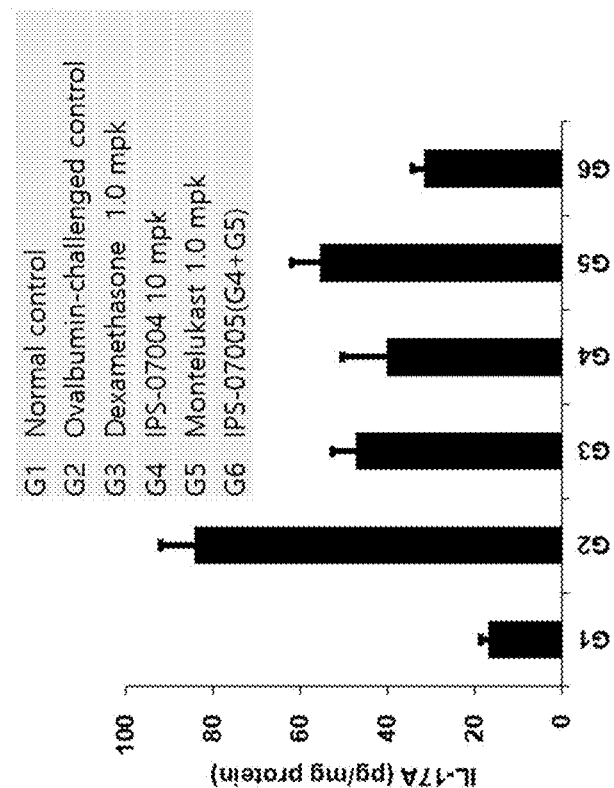
FIGS. 16A and 16B. Inhibitory effect of IPS-07005 on expression of IL17A and CXCL1 in BAL fluid.
Figure 17A:
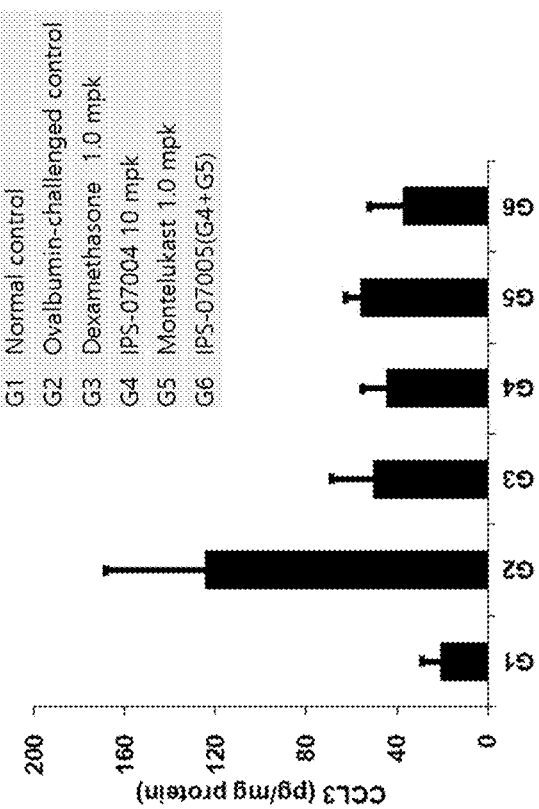
FIGS. 17A and 17B. Inhibitory effect of IPS-07005 on expression of CCL3 and CCL2 in BAL fluid.
Figure 17B:
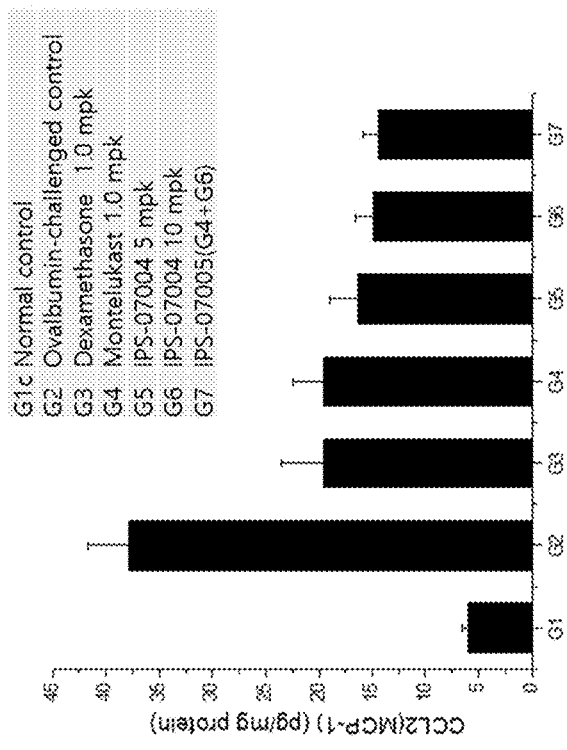

FIG. 16 shows the inhibitory effect of IPS-07005 on expression of IL17A and CXCL1 in BAL fluid. FIG. 17 shows the inhibitory effect of IPS-07005 on expression of CCL3 and CCL2 in BAL fluid.

To determine the anti-asthmatic effect of IPS-07005 on cytokine levels in mice with asthma, IL-17A, CXCL1, CCL2, and CCL3 production in BAL fluid was measured. Exposure to OVA caused a marked increase of IL-17A, CXCL1, CCL2, and CCL3 in BAL fluid compared with the mice in the normal group (FIGS. 16 and 17). However, the levels of IL-17A, CXCL1, which play an important role in neutrophil infiltration, in BAL fluid following OVA exposure were decreased in the presence of IPS-07005 in OVA-exposed mice (FIG. 16).

This result strongly suggested that IPS-07005 can suppress neutrophilic asthma, which is a medical unmet need for treating asthma. The levels of CCL2 and CCL3, which play a key role in macrophage activity in BAL fluid were decreased by IPS-07005 (FIG. 17). It appeared to be more effective in reducing the expression of these cytokines compared to IPS-07004 or Montelukast. The inhibitory effect of IPS-07005 on the expression of these cytokines is due to the synergistic function of IPS-07004 and Montelukast. Taken together, these findings demonstrate that the anti-inflammatory effect of IPS-07005 is mediated by the regulation of multiple inflammatory factors.

Methods 25 mg Ovalbumin (OVA) and 1 mg aluminum hydroxide hydrate (AlOH3) were dissolved in 300 mL of sterile saline solution and sensitized by intraperitoneal administration at 0 and 21 days. At the end of the observation period, all living animals were anesthetized using Isoflurane, and blood was collected from the vena cava/abdominal aorta. Lungs are removed and washed with sterile saline solution. 250 mL of sterile saline was filled in a 1 mL syringe, and the injection and recovery were repeated three times. The washed solution was lightly centrifuged (300 rpm, 10 minutes) and the supernatant was frozen and used for analysis of CXCL1 (ab216951, Abcam PLC) IL-17A (ab199081, Abcam PLC) and CCL3 (ab100726, Abcam PLC). The precipitate was resuspended in the same amount of sterile saline solution and used for eosinophil count and total cell count. The collected blood was left at room temperature for 30 minutes and centrifuged at 3,000 rpm for 20 mins. to separate serum and used for total IgE and Ova-specific IgE analysis. Histopathological examination was performed using lung tissue fixed in formalin. Lung tissues extracted at autopsy were placed in a cassette and submerged in 10% Neutral buffered formalin (10% NBF) at least 20 times the tissue volume. After fixation, the tissue was cut to about 4 mm in thickness and fabricated into paraffin blocks after general tissue treatment and embedding. After that, the slice was cut to 4 μm thickness using a rotary microtome, and Hematoxylin & Eosin (H&E) staining and PAS staining were performed.

Example 7. Inhibition of Parkinson's Disease

Methods

For 1-methyl-4-phenyl-1,2,3,6-tetrahydropyridine (MPTP) intoxication, the mice received four intraperitoneal (i.p.) injections of MPTP-HCl (20 mg/kg, free base in saline; Sigma-Aldrich, St. Louis, Mo.) dissolved in PBS at 2 h intervals. Twelve hours after the last MPTP injection, the MPTP-injected mice were received IPS-07004, Montelukast, or IPS-07005 once daily through p.o. administrations.

Figure 18:
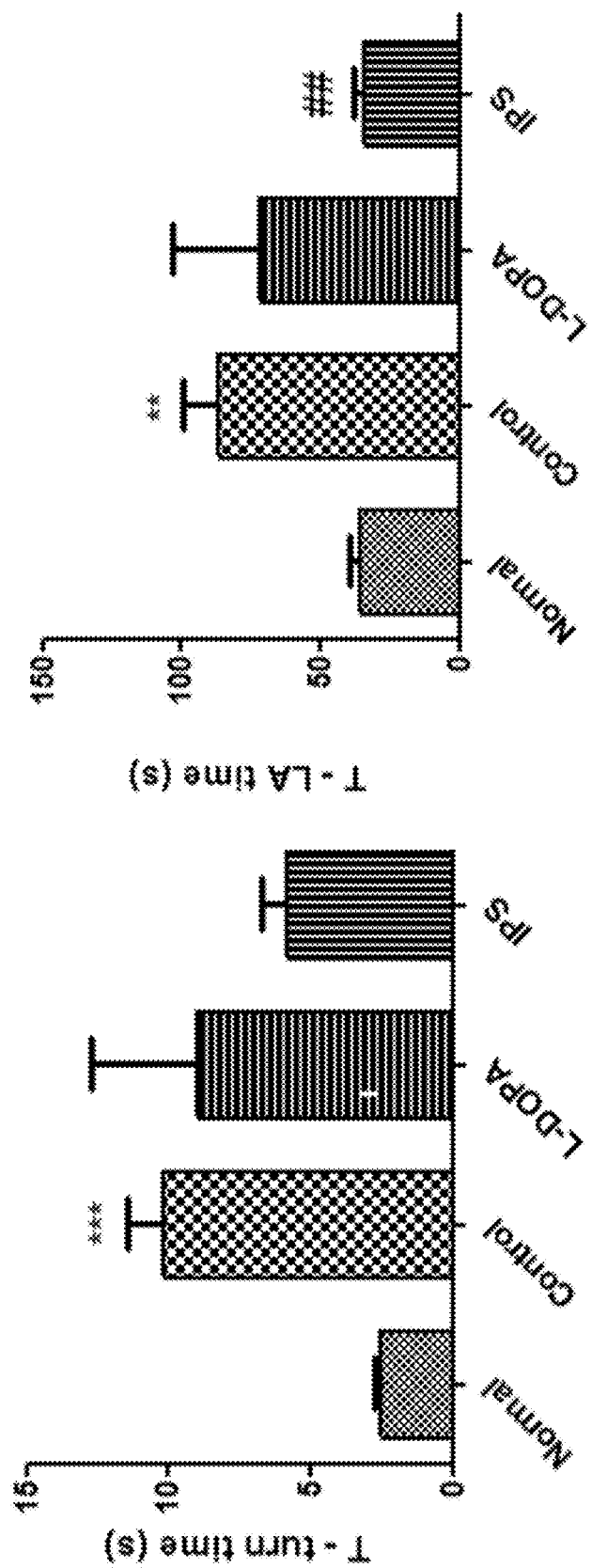
FIG. 18. Effect of IPS-07004 on behavior of Parkinson's disease (PD) mice.

To examine the effect of IPS-07004 on abnormal behavior of PD mice, Pole test (T-turn and T-LA time) was carried out. PD was induced in mice treated with MPTP (20 mg/kg, I.P) and the mice were administered with IPS-07004 at a dose of 10 mg/kg. And then pole test was performed in the mice. which can measure bradykinesia, a hallmark of Parkinson's disease. The T-turn measures the time the black mouse turns down from the top of the pole. IPS-07004 reduced the T-turn and T-LA time compared with MPTP-treated control group and L-Dopa-treated group, as shown in FIG. 18.

Figure 19:
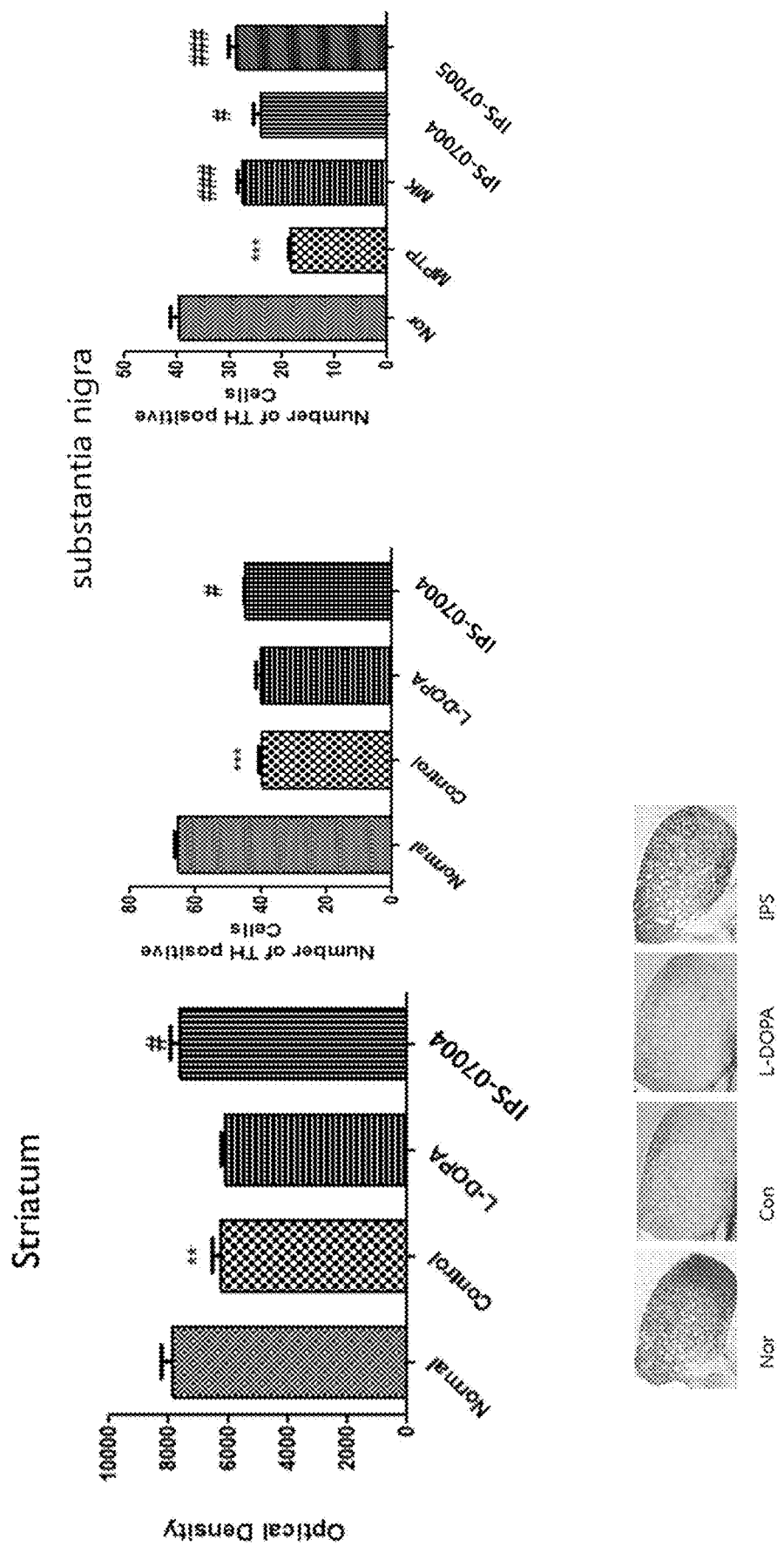
FIG. 19. Effect of IPS-07005 on the expression of tyrosine hydroxylase in striatum and substantia nigra in PD brain.

To determine the anti-PD function of IPS-07004 and IPS-07005 in PD mice, we analyzed the expression of tyrosine hydroxylase (TH) in striatum and Substantia nigra in PD brain. Immunohistochemical analysis in the brain showed that TH level was decreased in IPS-07004 and 07005-treated mice compared with MPTP-treated control group and L-Dopa-treated group, as shown in FIG. 19.

Figure 20:
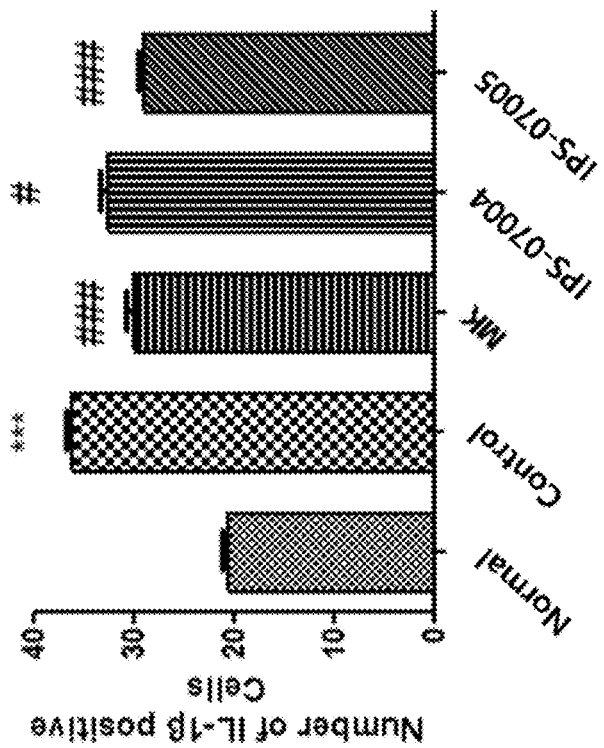
FIG. 20. Effect of IPS-07005 on the expression of IL-1$\beta$ in PD brain.
Figure 20:
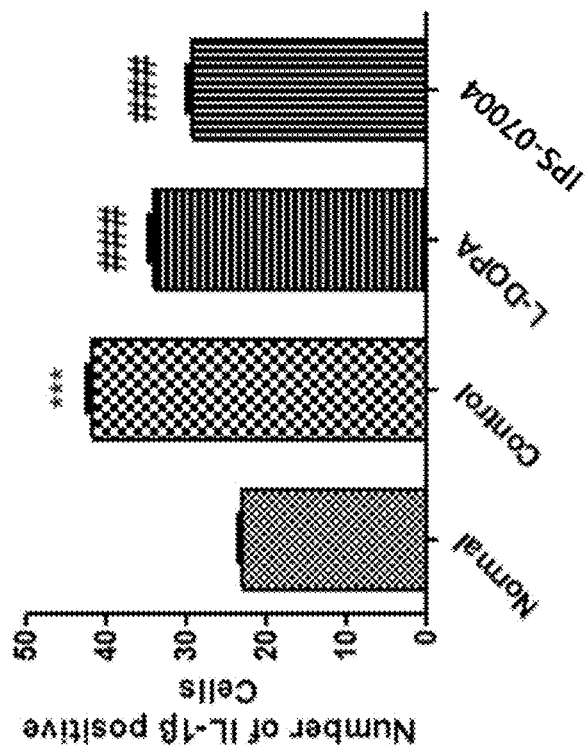

To assess whether the anti-PD function of IPS-07004 and 07005 is due to inhibit inflammation in PD brain, the analysis of cytokine expression was performed. IPS-07004 and IPS-07005 reduced IL-1b expression in PD mice, as shown in FIG. 20.

The foregoing description of the specific embodiments will so fully reveal the general nature of the invention that others can, by applying knowledge within the skill of the art, readily modify and/or adapt for various applications, without departing from the general concept of the invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed is:

1. A method of treating asthma in a subject in need thereof, the method comprising administering to the subject a pharmaceutical composition comprising a compound represented by Formula 1 or a pharmaceutically acceptable salt thereof and a pharmaceutically acceptable excipient:

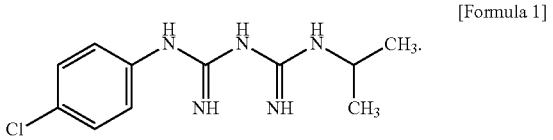 [SMILES: CC(C)NC(=N)NC(=N)Nc1ccc(Cl)cc1]

[Formula 1]

2. The method of claim 1, wherein the composition further comprises a compound represented by Formula 2 or a pharmaceutically acceptable salt thereof:

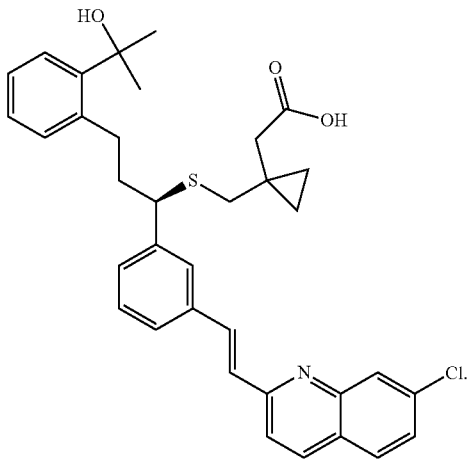

[Formula 2]

3. The method of claim 1, wherein the asthma is allergen-induced asthma, viral-induced asthma, cold-induced asthma, pollution-induced asthma and/or exercise-induced asthma.

4. The method of claim 2, wherein the asthma is allergen-induced asthma, viral-induced asthma, cold-induced asthma, pollution-induced asthma and/or exercise-induced asthma.

5. The method of claim 1, wherein the composition is administered orally to the subject.

6. The method of claim 2, wherein the composition is administered orally to the subject.

7. The method of claim 1, wherein the composition comprises 0.001 mg to 100 mg of each of the compound per kg of the subject's body weight.

8. The method of claim 2, wherein the composition comprises 0.001 mg to 100 mg of each of the compound per kg of the subject's body weight.

* * * * *